US009486176B2

(12) United States Patent
Goyal

(10) Patent No.: US 9,486,176 B2
(45) Date of Patent: Nov. 8, 2016

(54) SYSTEMS AND METHODS FOR DIAGNOSING STROKES

(71) Applicant: Mayank Goyal, Calgary (CA)

(72) Inventor: Mayank Goyal, Calgary (CA)

(*) Notice: Subject to any disclaimer, the term of this patent is extended or adjusted under 35 U.S.C. 154(b) by 0 days.

(21) Appl. No.: 15/040,578

(22) Filed: Feb. 10, 2016

(65) Prior Publication Data

US 2016/0157800 A1 Jun. 9, 2016

Related U.S. Application Data

(63) Continuation-in-part of application No. 14/425,763, filed as application No. PCT/CA2013/000761 on Sep. 4, 2013, now Pat. No. 9,324,143.

(60) Provisional application No. 61/697,282, filed on Sep. 5, 2012.

(51) Int. Cl.
| | | |
|---|---|---|
| *G06K 9/00* | (2006.01) | |
| *A61B 6/00* | (2006.01) | |
| *A61B 6/03* | (2006.01) | |
| *G06T 7/00* | (2006.01) | |
| *A61B 8/00* | (2006.01) | |

(52) U.S. Cl.
CPC .............. *A61B 6/501* (2013.01); *A61B 6/032* (2013.01); *A61B 6/481* (2013.01); *A61B 6/486* (2013.01); *A61B 6/504* (2013.01); *A61B 6/507* (2013.01); *A61B 6/5217* (2013.01); *G06T 7/0016* (2013.01); *G06T 2207/10081* (2013.01); *G06T 2207/20021* (2013.01); *G06T 2207/30016* (2013.01)

(58) Field of Classification Search
USPC ....... 382/100, 103, 107, 128–134, 162, 168, 382/173, 181, 209, 219, 232, 254, 274, 382/286–291, 294, 305, 312; 424/9.45; 600/437, 407, 454; 703/11; 358/3.26; 378/4, 21
See application file for complete search history.

(56) References Cited

U.S. PATENT DOCUMENTS

| | | | |
|---|---|---|---|
| 6,650,928 B1 | 11/2003 | Gailly et al. | |
| 7,580,737 B2 * | 8/2009 | Wintermark | A61B 5/0275 600/407 |
| 8,019,142 B2 | 9/2011 | Nowinski et al. | |
| 8,050,475 B2 | 11/2011 | Nowinski | |
| 8,116,542 B2 * | 2/2012 | Avinash | G06K 9/00 382/128 |

(Continued)

OTHER PUBLICATIONS

Khatri et al. Time to angiographic reperfusion and clinical outcome after acute ischaemic stroke: an analysis of data from the interventional management of stroke (IMS III) phase 3 trial. Lancet Neurol 2014; 13:567-74.
Broderick et al. Endovascular Therapy after Intravenous t-PA versus t-PA Alone for Stroke. N Engl J Med 2013;368:893-903.

(Continued)

*Primary Examiner* — Seyed Azarian
(74) *Attorney, Agent, or Firm* — McGlew and Tuttle, P.C.

(57) ABSTRACT

The invention relates to systems and methods for diagnosing strokes. In particular, systems and methods for acquiring timely patient status information are described that enable a physician to make diagnostic and treatment decisions relating to ischemic and hemorrhagic strokes. The systems and methods enable the efficient and quantitative assessment of arterial collaterals within the brain for aiding these decisions in the case of ischemic strokes. In the case of hemorrhagic strokes, the systems and methods are effective in determining if there is a leak and what is the rate of leaking. The systems and methods of the invention can be used to improve the accuracy and confidence of ASPECTS.

10 Claims, 13 Drawing Sheets

(56) References Cited

U.S. PATENT DOCUMENTS

| | | | |
|---|---|---|---|
| 8,155,466 B2* | 4/2012 | Licato | G06T 5/10 358/3.26 |
| 8,233,684 B2 | 7/2012 | Licato et al. | |
| 2002/0161292 A1 | 10/2002 | Wintermark et al. | |
| 2005/0113680 A1 | 5/2005 | Ikeda et al. | |
| 2006/0004279 A1 | 1/2006 | Ikeda et al. | |
| 2006/0222142 A1 | 10/2006 | Kudo | |
| 2007/0129627 A1 | 6/2007 | Profio et al. | |
| 2008/0312533 A1* | 12/2008 | Balberg | A61B 5/14546 600/437 |
| 2009/0034812 A1 | 2/2009 | Nowinski et al. | |
| 2009/0232373 A1 | 9/2009 | Licato et al. | |
| 2010/0128942 A1 | 5/2010 | Licato et al. | |
| 2010/0158337 A1 | 6/2010 | Buerger et al. | |
| 2011/0015520 A1 | 1/2011 | Meetz et al. | |
| 2011/0038517 A1 | 2/2011 | Mistretta et al. | |
| 2011/0103671 A1 | 5/2011 | Meetz et al. | |
| 2011/0150309 A1 | 6/2011 | Barfett et al. | |
| 2011/0229003 A1 | 9/2011 | Yang | |
| 2011/0295113 A1 | 12/2011 | Profio et al. | |
| 2011/0311457 A1* | 12/2011 | Skerrett | A61K 49/0485 424/9.45 |
| 2012/0053921 A1* | 3/2012 | Taylor | A61B 5/02007 703/11 |

OTHER PUBLICATIONS

Saver, Jeffrey L. Time is Brain-Quantified. Stroke 2006;37:263-266.

Saver et al. Stent-retriever thrombectomy after intravenous t-PA vs. t-PA alone in stroke. N Engl J Med Apr. 17, 2015.

Jovin et al. Thrombectomy within 8 hours after symptom onset in ischemic stroke. N Engl J Med Apr. 17, 2015.

Goyal et al. Randomized assessment of rapid endovascular treatment of ischemic stroke. N Engl J Med. Feb. 11, 2015.

Goyal et al. Consistently achieving computed tomography to endovascular recanalization <90 minutes: solutions and innovations. Stroke Oct. 28, 2014; 45:e252-e256.

Menon et al. Optimal workflow and process-based performance measures for endovascular therapy in acute Ischemic stroke: analysis of the solitaire FR thrombectomy for Acute Revascularization Study. Stroke 2014;45:00-00.

Menon et al., Multiphase CT Angiography: A New Tool for the Imaging Triage of Patients with Acute Ischemic Stroke, Radiology: vol. 000: No. 0, 2015.

* cited by examiner

Time to Reperfusion and Good Clinical Outcome

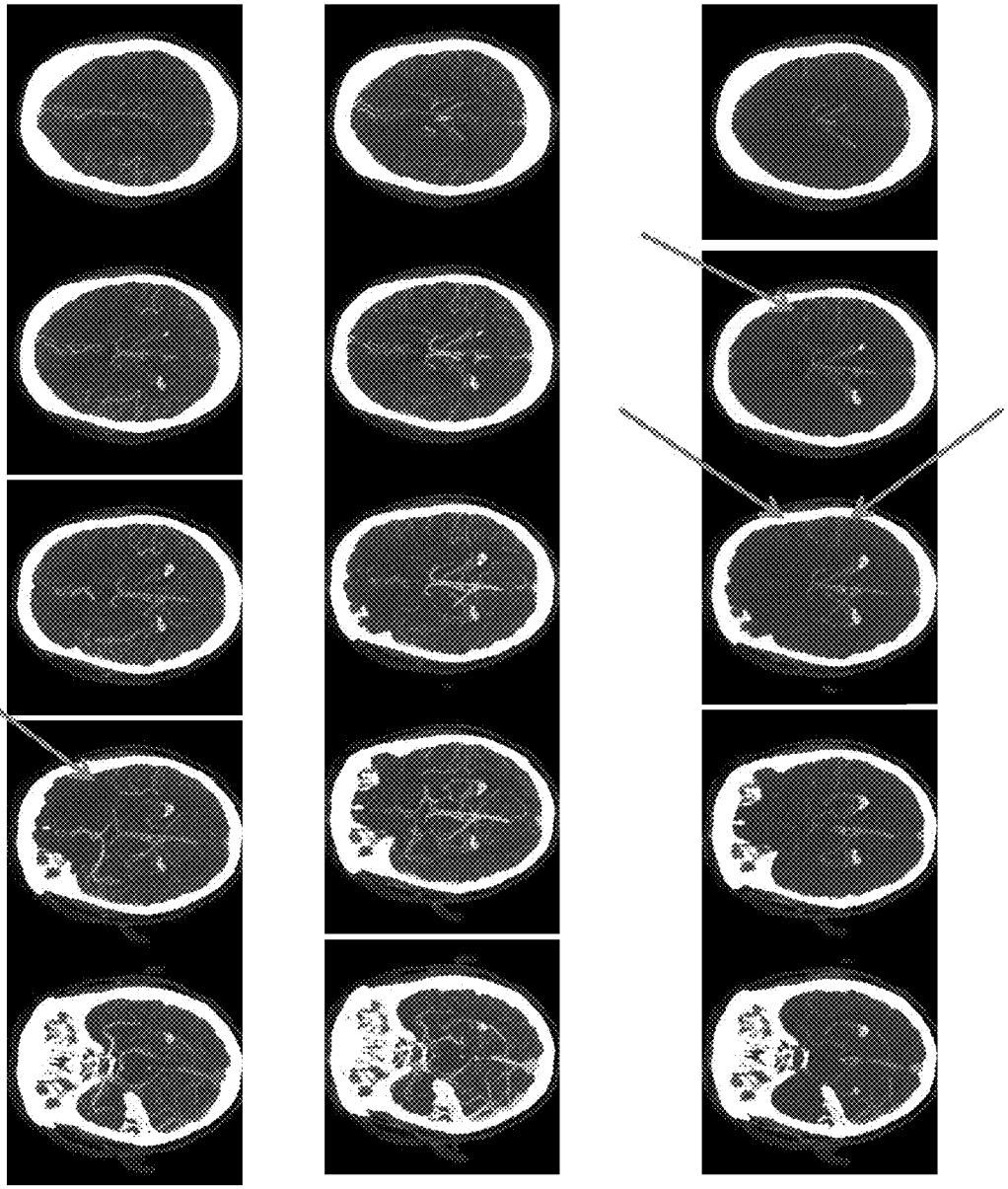

SYSTEMS AND METHODS FOR DIAGNOSING STROKES

FIELD OF THE INVENTION

The invention relates to systems and methods for diagnosing strokes. In particular, systems and methods for acquiring timely patient status information are described that enable a physician to make diagnostic and treatment decisions relating to ischemic and hemorrhagic strokes. The systems and methods enable the efficient and quantitative assessment of arterial collaterals within the brain for aiding these decisions in the case of ischemic strokes. In the case of hemorrhagic strokes, the systems and methods are effective in determining if there is a leak and what is the rate of leaking. The systems and methods of the invention can be used to improve the accuracy and confidence of ASPECTS.

BACKGROUND OF THE INVENTION

Ischemic stroke is an acute disease where tissue death (infarction) within the brain of different patients will progress at different rates from the time of the ischemic event. The rate of infarction within a patient depends on a large number of physiological factors.

For the physician diagnosing and treating ischemic strokes, when a stroke patient arrives at a hospital, it is very important for the physician to obtain as much knowledge about the nature of the stroke as soon as possible in order to make an effective diagnosis and effective decisions regarding treatment. As is readily understood, time to effect diagnosis and treatment is very important as faster diagnoses will impact treatment decisions and can minimize the amount of brain tissue that is ultimately affected as a result of the stroke.

For example, in the case of an ischemic stroke, it is important for the physician to know where the vessel occlusion is, how big the occlusion is, where any dead brain tissue (termed "core") is and, how big and where is the brain tissue that may have been affected by the ischemic event but that may potentially be saved (this tissue is termed "penumbra").

More specifically, the penumbra is tissue around the ischemic event that can potentially stay alive for a number of hours after the event due to perfusion of this tissue by collateral arteries. That is, the collateral arteries may provide sufficient oxygen to the penumbra tissue to prevent this tissue from dying for a period of time.

When the physician has good information about the collaterals and how the collaterals may be located in and around the penumbra, treatment decisions can be made that can significantly affect patient outcomes.

Importantly, in an emergency or acute situation, the process of making a decision will consider the amount of information at a given moment in time. That is, a definitive 'yes' decision can be made to take action or a 'no' decision can be made to take no action based on the current information. In addition, a third decision choice can be made to wait for additional information. In the situation of acute stroke (and other emergency scenarios), time to make a definitive diagnostic/treatment decision must be balanced against the likelihood of a negative outcome that results simply from the delay in making a decision. In other words, the decision to wait for more information must consider what the effects of a delay in making a decision might be.

In the specific case of acute ischemic stroke, the pace or rate of neural circuitry loss in a typical large vessel supratentorial acute ischemic stroke is shown in Table 1.

TABLE 1

Estimated Pace of Neural Circuitry Loss in Typical Large Vessel, Supratentorial Acute Ischemic Stroke (3)
Estimated Pace of Neural Circuitry Loss in Typical Large Vessel, Supratentorial Acute Ischemic Stroke

|  | Neurons Lost | Synapses Lost | Myelinated Fibers Lost | Accelerated Aging |
|---|---|---|---|---|
| Per Stroke | 1.2 billion | 8.3 trillion | 7140 km/4470 miles | 36 yrs |
| Per Hour | 120 billion | 830 billion | 714/447 miles | 3.6 yrs |
| Per Minute | 1.9 million | 14 billion | 12 km/7.5 miles | 3.1 weeks |
| Per Second | 32,000 | 230 million | 200 meters/218 yards | 8.7 hours |

As can be seen, delays in making a decision in the order of only a few minutes can have a significant impact on patient outcome in terms of neural circuitry loss. Moreover, and as shown in FIGS. 1 and 2, a better outcome is significantly more likely to occur when the decision to treat is made earlier. As shown in FIG. 1, whether or not a treatment is ultimately beneficial or not may depend on when the decision to treat is made. As shown in FIG. 1, treatment decision times A, B, C, D will each have a different affect on the relative number of neurons that could be saved. That is, if a treatment decision is made at time A (i.e. an earlier time), if it is assumed that the pace of neural circuitry loss is linear (assumed only for this example), a greater number of neurons can be saved. As the time of making the treatment decision is delayed, the likelihood of the treatment being beneficial will decrease until it is uncertain whether the treatment will be beneficial (i.e. at times B and C) or where there is a high likelihood that the treatment will be of no value (i.e. at time D).

Further, FIG. 2 illustrates the effect of time to reperfusion and good clinical outcome for observed cases where the abscissa shows time from stroke to reperfusion and the ordinate shows the probability of the patient achieving a post-treatment mRS score of 0-2. Table 2 shows the time to reperfusion and good clinical outcome for the data of FIG. 2 (1).

TABLE 2

Time to Reperfusion and Good Clinical Outcome

|  | Risk Ratio | 95% CI | p-value |
|---|---|---|---|
| Time to Reperfusion (every 30 minutes) | 0.86 | 0.78-0.95 | P = 0.0045 |

At the present time, in many treatment centers, when a stroke patient arrives, the assessment protocol is generally as follows:
  a. Conduct a CT scan of the head to rule out or look for evidence of a hemorrhagic stroke.
  b. Conduct a CT angiogram (CTA) to locate the site of vessel occlusion.
  c. Conduct a CT perfusion (CTP) study to create perfusion maps that provide the physician with information about various parameters including cerebral blood flow, cerebral blood volume and mean transit time.

As is known, each of these generalized steps will be affected by a large number of factors and the time to complete each of them will be variable from patient to patient and between different treatment centers. For example, such factors may include resource availability (eg. trained medical staff and equipment) as well as processing times required by CT scan equipment and other ancillary hardware and software to present data to physicians.

For the purposes of illustration, these factors are described in terms of a representative diagnosis and treatment scenario of a patient exhibiting symptoms of a stroke, the patient arriving at the emergency room of a treatment center and who thereafter receives the above CT procedures as part of the diagnostic protocol. Table 3 summarizes a number of the key process steps and typical times that may be required to complete each step.

Upon arrival at the treatment center, an emergency room physician conducts a preliminary assessment of the patient. If the preliminary assessment concludes a potential stroke, the patient is prepared for a CT scan. The time taken to initially assess a potential stroke patient upon arrival at the treatment facility may be 3-5 minutes.

Preparing the patient for a CT scan involves a number of steps including transferring the patient to the CT imaging suite and connecting an intra-venous line to the patient to enable the injection of contrast agent into the patient during the various CT procedures.

The CT scan includes conducting an x-ray scan of the patient together with a computerized analysis of the x-ray data collected. More specifically, as is known, during a CT scan, beams of x-rays are emitted from a rotating device through the area of interest in the patient's body from several different angles to receivers located on the opposite sides of the body. The received data is used to create projection images, which are then assembled by computer into a two or a three-dimensional picture of the area being studied. More specifically, the computer receives the x-ray information and uses it to create multiple individual images or slices which are displayed to the physician for examination.

CT scans require that the patient hold still during the scan because significant movement of the patient will cause blurred images. This is sometimes difficult in stroke patients and hence sometimes head restraints are used to help the patient hold still. Complete scans take only a few minutes.

Upon completion of the initial CT scan including the post-processing time to assemble the images, the physician interprets the images to determine a) if a stroke has occurred and, b) if so, to determine if the stroke is hemorrhagic or ischemic. If the stroke is hemorrhagic, different procedures may be followed. It will typically take the physician in the order of 1-2 minutes from the time the images are available to make the determination that the stroke is hemorrhagic or ischemic.

If the stroke is ischemic, the decision may be made to conduct a CT angiogram (CTA).

CT angiography procedures generally require that contrast agents be introduced into the body before the scan is started. Contrast is used to highlight specific areas inside the body, in this case the blood vessels. In addition because of presence of contrast in the very small vessels of the brain, overall the brain looks brighter (has a higher Hounsfield value) also known as contrast enhancement. Contrast agents are iodine based compounds that inhibit the passage of x-rays through the tissue. As such, they can be effective in enhancing the distinction between tissues where the contrast agent is present compared to those tissues where it is not. The CT angiogram requires additional preparation time but will typically not require that the patient be moved. Generally, CT angiogram procedures involve the injection of a bolus of contrast through an IV line followed by the CT scan. A typical contrast bolus may be 70-100 ml injected at 5 ml/second. The volume and injection rate of contrast is determined by the procedure being followed and is generally injected in a minimally sufficient volume to be present in the tissues of interest at the time the CT scan is conducted. Over a relatively short time period, the contrast becomes diffused within the body thereby providing only a relatively short window of time to conduct a CT procedure.

The CT angiogram data is substantially greater than what is collected from a basic scan and like a basic CT scan must be subjected to post-processing to create the images. The post-processing time is typically in the range of 3-5 minutes.

After processing, the physician interprets the data and makes a decision regarding treatment. Generally, the physician is looking to determine a) where is the occlusion? b) what is the size of the core? and c) obtain a qualitative feel for penumbra and collaterals.

Ultimately, and based on these factors, the physician is looking to make a decision on what brain tissue is worth fighting for. In other words, based on the combination of all these factors, the physician is looking to decide either that very little or no penumbra can be saved, or alternatively that it appears that penumbra can be saved and it is worthwhile to do so.

The CT angiogram provides relatively little data about collaterals and perfusion to the ischemic tissue as it is only a picture of the brain at one instance in time. That is, as it takes time for contrast agent to flow through the brain tissues and such flow will be very dependent on the ability of vessels to carry the contrast agent, a single snapshot in time does not give the physician enough information to make a diagnostic and/or treatment decision. Hence, CT perfusion (CTP) procedures may be undertaken to give the physician a more quantitative sense of brain perfusion. Like CT angiogram, CT perfusion procedures involve the injection of contrast agent into the patient. It should also be noted that some centers may choose to do a CT perfusion study before the CT angiogram because they feel that the contrast injection from the CT angiogram interferes with the quality of data of the CT perfusion.

Perfusion computed tomography (CTP) allows qualitative and quantitative evaluation of cerebral perfusion by generating maps of cerebral blood flow (CBF), cerebral blood volume (CBV), and mean transit time (MTT). The technique is based on the central volume principle (CBF=CBV/MTT) and requires the use of complex software employing complex deconvolution algorithms to produce perfusion maps. Other maps such as Tmax maps may also be created.

CTP studies are acquired with repeated imaging through the brain while the contrast is injected. The technique varies significantly from vendor to vendor and also from center to center and hence requires specialized training with the specific equipment at each center. CTP typically involves imaging of the brain over approximately 60-70 seconds (at 1-4 second intervals) in order to acquire multiple images. The technique is quite vulnerable to patient motion and also requires the patient to hold still for the period. Furthermore, CTP also involves substantial radiation exposure in the range of 5-10 mSv as the number of images taken over the time period is significant.

The procedure generates a large dataset that must then be transferred to a dedicated workstation for post-processing. This step may take over 10 minutes in order to produce separate maps of each of CBF, CBV, and MTT. The perfusion maps are typically color coded maps.

Importantly, the post-processing requires the use of specialized and very often proprietary software that must be run by trained individuals. Ultimately, the time taken to fully complete CTP acquisition and analysis is highly variable as the above factors including the vendor, the speed of data transfer, local expertise, the time of day the study is being undertaken (i.e. working hours vs. after hours) as well as other factors can all have an affect on the actual amount of time required to complete the study.

TABLE 3

Typical Diagnostic Steps and Completion Times

| Procedure | Time (minutes) | Elapsed Total | Comments |
|---|---|---|---|
| Initial Assessment | 3-5 | 3-5 | |
| Transfer and Preparation for CT Scan | 20 | 23-25 | |
| CT Scan | 1 | 24-26 | |
| CT Scan Interpretation and CT Angiogram Preparation | 2-3 | 26-30 | CT Angiogram Preparation may be concurrent with CT Scan Interpretation |
| CT Angiogram Procedure | 1-3 | 27-33 | |
| CT Angiogram Post Processing | 2 | 29-35 | |
| CT Angiogram Interpretation and CT Perfusion Preparation | 4 (minimum) | 33-39 | CT Perfusion Preparation may be concurrent with CT Scan Interpretation |
| CT Perfusion Procedure | 1 | 34-40 | |
| CT Perfusion Post Processing | Variable 5-20 (minimum) | 44-60 | Will depend on vendor specifics |
| CT Perfusion Interpretation | Variable 2-10 (minimum) | 46-70 | Will depend factors including: time of day; center; vendor equipment etc. |

Thus, while perfusion CT is not a perfect technique, it has been found to be useful for noninvasive diagnosis of cerebral ischemia and infarction as it does provide some degree of quantitative determination of core and penumbra. However, as noted above, there are problems with these procedures. In summary, these problems include:
  a. CT perfusion takes time to complete (8-30+ minutes total).
  b. Patient motion can affect results.
  c. Significant post-processing time is required to complete a full perfusion map.
  d. Additional radiation exposure to the patient.
  e. Need for additional contrast agents.
  f. Non-standardized procedures for completing the perfusion map.
  g. Variations in technique with different vendor equipment.
  h. Lack of consensus in the medical community regarding the interpretation and best practices for treatments based on the CT perfusion maps.
  i. Lack of information regarding rate of infarct growth.
  j. Significant variability across vendors for the degree of coverage of the brain (eg. 4 to 16 cms). Also some vendors have the option of covering 8 cm using a 'toggle table' technique that may introduce additional errors.

As a result, notwithstanding the benefits of CTP, there continues to be a need for improved procedures and systems that can address these problems that provide the physician with the ability to make faster diagnoses. Most importantly, there has been a need for improved systems for assessing patient collaterals after ischemic stroke and, in particular, the need to create a fast and reproducible collateral map as opposed to a perfusion map. Further still, there has been a need for systems and methods that enable faster recanalization in order to increase the chances of saving penumbra tissue given the rate of neural death in a typical large vessel ischemic stroke.

In addition, there has also been a need for systems and methods that can be consistently implemented at different treatment centers and across different CT machines (i.e. from different vendors) that reduce the level of specialized and/or advanced training that may be required to provide a consistent and accurate diagnosis.

Further still, there has also been a need for systems and methods that enable the identification and quantification of parameters about the blood clot/thrombus causing an ischemic stroke. That is, in proximal artery occlusion it is helpful to the endovascular surgeon to understand more about the nature of the clot causing the stroke and more specifically know the exact length of the clot and its relative permeability and/or porosity which will aid in treatment decisions.

With regards to hemorrhagic strokes, there is similarly a need for systems and systems methods that enable faster diagnoses with enough information to assist in making treatment decisions.

ASPECTS

In addition, in recent years, stroke physicians have been utilizing a semi-quantitative method for determining the amount of dead brain during the diagnostic processes of ischemic stroke. ASPECTS (Alberta Stroke Program Early CT Score) is a 10 point scoring system that allows physicians utilize to provide a graded score on the relative severity of a stroke. Generally, the lower the ASPECTS score, the greater the severity of the stroke in terms of the amount of dead brain whereas a higher score indicates less brain tissue has died. A more detailed explanation of the ASPECTS system can be found at www.aspectsinstroke.com (incorporated herein by reference). In the context of this description, ASPECTS is defined as the accepted protocol as of the filing date of this application (4).

Generally, ASPECTS was developed to offer the reliability and utility of a standard CT examination with a reproducible grading system to assess early ischemic changes on pretreatment CT studies in patients with acute ischemic stroke of the anterior circulation. It is determined from evaluation of two standardized regions of the MCA territory: the basal ganglia level, where the thalamus, basal ganglia, and caudate are visible, and the supraganglionic level, which includes the corona radiata and centrum semiovale using non-contrast CT data. All cuts with basal ganglionic or supraganglionic structures visible are required to determine if an area is involved. The abnormality should be visible on at least two consecutive cuts to ensure that it is truly abnormal rather than a volume averaging effect To compute the ASPECTS, 1 point is subtracted from 10 for any evidence of early ischemic change for each of the 5 defined regions. A normal CT scan receives ASPECTS of 10 points and a score of 0 indicates diffuse involvement throughout the MCA territory.

Axial NCCT images showing the MCA territory regions as defined by ASPECTS. C—Caudate, I—Insularribbon, IC—Internal Capsule, L—Lentiform nucleus, M1—Anterior MCA cortex, M2—MCA cortex lateral to the insular ribbon, M3—Posterior MCA cortex, M4, M5, M6 are the anterior, lateral and posterior MCA territories immediately superior to M1, M2 and M3, rostral to basalganglia. Subcortical structures are allotted 3 points (C, L, and IC). MCA cortex is allotted 7 points (insular cortex, M1, M2, M3, M4, M5 and M6)

As noted, ASPECTS is an important method of standardizing or grading the severity of a stroke and over the past number of years has become accepted as the standard by which stroke physicians communicate about the relative severity of strokes. It has been used effectively in recent trials and also as a means of selecting patients for trials to the extent that the guidelines for stroke care have changed across the world. For example, in the United States, guidelines state that, amongst other factors, patients with an ASPECTS score greater than 5 are suitable candidates for endovascular treatment The method of determining an ASPECTS score is somewhat subjective in that it relies of the qualitative assessment made by one or more physicians based on empirical data. Analysis of the various errors sources of error can be generally categorized into imaging quality errors and interpretation errors.

In the case of imaging errors, factors including the age and nature of the scanning equipment, set-up and operation (eg. radiation levels) can affect the images and hence their interpretation. Also, imaging errors can be a result of patient errors include factors such as patient movement, the presence of old infarcts, age of the patient and related factors such atrophy and microangiopathic disease can also affect interpretation.

Image interpretation can be affected by a lack of adequate training including the availability of expertise at a particular facility as well as the pressure physicians may be under during an emergency and the speed with which decisions may be made.

Recently, there have been attempts to reduce the subjectivity factors in image interpretation through the use of computer algorithms to provide an ASPECTS score from images. A prior art system (Brainomix, Oxford, UK) provides a software system that automates the ASPECTS score from non-contrast CT data. However, at the present time, there is not acceptance that the ASPECTS scores that this software provides are equally or more reliable than physician determined ASPECTS.

That is, there is criticism of this system on the basis that it is not capable of discerning whether the images it is assessing are acceptable images and hence, it will make a determination that does not properly address the quality of the data it is using to make a decision. Importantly, the Brainomix system does not utilize the contribution of collaterals to ASPECTS.

As such many such automated algorithms lack precision and/or specificity e.g. depending on the situation especially in a patients presenting very early, an automated software may be able to say that the ASPECTS is somewhere between 4 to 8: this range is such that it does not permit good decision making (following the American Guidelines). Alternatively the software may be able to calculate (depending on how the algorithm is set up) ASPECTS to state e.g. ASPECTS score of 7 with 60% precision. This again would not allow for good and efficient decision making.

Accordingly, there has been a need for systems and methods that more accurately and more reliably can automate ASPECTS and that utilize the contribution of collateral blood flow to ASPECTS.

Further, biologically it makes sense that poor collaterals will correlate to poorer ASPECTS, since it is blood flow through the collaterals that keep the brain alive.

Based on the pathophysiology and experience, the ASPECTS grading and the collateral grading go hand in hand. There are very few exceptions. These include the situation where the patient is being imaged very quickly after stroke onset where the images show poor collaterals but brain changes (i.e death) hasn't set in yet. Another situation is the patient who at some time went into hypotension/shock before reaching the imaging suite with the result being that the blood supply dropped, the brain died meaning that a poor ASPECTS should be assessed, but prior to subsequent imaging, the blood pressure improved so that by the time the imaging was completed, the collaterals were strong.

As a result, there has been a need for improved systems and methods to automatically calculate ASPECTS with improved accuracy and confidence and more specifically utilizes collateral data.

SUMMARY OF THE INVENTION

In accordance with the invention, systems and methods for diagnosing strokes are described. The systems and methods described herein enable faster diagnoses and treatments of different types of strokes by providing a physician with effective and timely information.

In accordance with a first aspect of the invention, a method of imaging the brain within a patient diagnosed as potentially suffering a stroke is described, the method for deriving information about blood flow within the brain the method comprising the steps of:
 a) injecting a bolus of contrast agent into the patient;
 b) obtaining a set of computed tomography (CT) images of the patient's brain at different levels at a specific time period, t, after step a);
 c) repeating step b) n times to obtain at least one additional set of CT images of the patient's brain at different levels at time period t after step b), wherein n is at least one and each set of CT images is defined as a phase of images, P1-Pn;
 d) displaying each phase of CT images from steps b) and c) as a time-sequenced series of images.

In various embodiments, the number of phases can be varied but preferably n is 1-6. The time period, t, can also be varied and may be selected based on a number of factors including the anticipated flow rate of contrast agent through the patient. The time period, t, may also be selected based on an initial diagnosis of the patient having suffered an ischemic or hemorrhagic stroke. For example, if the patient is suspected as having suffered an ischemic stroke, t will typically be 6-18 seconds. If the patient is suspected as having suffered a hemorrhagic stroke the time period t, is preferably 10-40 seconds.

In another embodiment, the method further comprises the step of: enabling a user to mark at least one zone of interest within one phase of the images to create a marked zone of interest and wherein a marked zone of interest represents any one of or a combination of asymptomatic tissue or symptomatic tissue. In one embodiment, a corresponding zone of interest of a single image on an opposite side of the brain is automatically marked based on the area and location of the at least one marked zone of interest. In one embodiment, a corresponding zone of interest in another phase is automatically marked to create further marked zones of interest based on the area and location of each marked zone of interest.

In another embodiment, the method further comprises the step of: calculating a contrast density value within each marked zone of interest. In one embodiment, contrast density values for each marked zone of interest are tabulated within a database.

In another embodiment, the method further comprises the step of: calculating and displaying a contrast density trend value from P1 to Pn for corresponding zones of interest across P1 to Pn on a symptomatic side.

In another embodiment, the method further comprises the step of: calculating and displaying a contrast density trend value from P1 to Pn for corresponding zones of interest across P1 to Pn on an asymptomatic side.

In a still further embodiment, the method further comprises the step of: comparing the contrast density trend value against a database of trend values to ascertain a collateral value for the marked zones across all phases.

In another embodiment, the method further comprises the step of: calculating and displaying a color code on at least one phase of images based on the collateral value or creating a colour coded map by summating the data from all the phases.

In another embodiment, the method further comprises the step of: calculating and displaying a change in contrast density of the entire brain from P1 to Pn.

In a still further embodiment, the method further comprises the steps of: identifying and marking one or more occlusions in one or more images in one or phases of the CT images and marking a downstream area relative to each marked occlusion; and, calculating and displaying a rate of opacification of vessels in the downstream area beyond each marked occlusion.

In yet another embodiment, the method further comprises the steps of: identifying and marking corresponding symptomatic and asymptomatic regions of the brain; and calculating, comparing and displaying contrast density trends from the marked symptomatic and asymptomatic regions of the brain.

In yet another embodiment, the method further comprises the steps of: identifying and marking the location of an occlusion; calculating the diameter of vessels distal to the occlusion; identifying corresponding vessels on the contralateral side; calculating the diameter of vessels on the contralateral side; and comparing and displaying the differences in vessel diameter for each side for each of P1 to Pn.

In one embodiment, if the patient is suspected as having suffered an ischemic stroke, a method of deriving information about the location and properties of a blood clot/thrombus is provided wherein after steps a) to d) are conducted, the method further comprising the steps of: enabling a user to mark a proximal end position of a suspected blood clot within at least one image of at least one phase of images; enabling a user to mark a distal end position of a suspected blood clot within at least one image of a later phase of images; and calculating and displayed a blood clot length based on the proximal and distal positions.

In one embodiment, if the patient is suspected as having suffered an ischemic stroke, a method of deriving information about the location and properties of a blood clot is provided wherein after steps a) to d) are conducted, the method further comprises the steps of: enabling a user to mark a proximal end area of a suspected blood clot/thrombus within at least one image of at least one phase of images; enabling a user to mark a distal end area of a suspected blood clot/thrombus within at least one image of a later phase of images; calculating and displayed a blood clot/thrombus volume based on the proximal and distal end areas.

In another embodiment, the method includes the step of calculating a rate of change of contrast density within an intravascular blood clot/thrombus volume across different phases and correlating the rate of change to a known rate of change of contrast density within a blood clot/thrombus volume to determine a blood clot/thrombus permeability.

In another embodiment, the method includes the step of calculating a rate of change of contrast density within a blood clot/thrombus volume across different phases to a known rate of change of contrast density within a blood clot/thrombus volume to determine a blood clot/thrombus porosity.

In another embodiment, if the patient is suspected as having suffered a hemorrhagic stroke, the method includes deriving information about the location of and rate of leak within a patient wherein steps a) to d) are conducted where t is 10-40 seconds and the method further comprising the steps of: enabling a user to mark a first instance of a suspected leak within the hematoma within each image of at least one phase of images wherein the user marks a border of the leak within the hematoma; calculating a first volume of the leak within the hematoma based on marked borders of the leak from the earliest phase of images showing the leak; repeating steps aa) and bb) for subsequent phases to calculate successive volumes of the leak; displaying each of the first volume and successive volumes; and, calculating the rate of leak and consequently the rate of increase of the hematoma over time.

In another aspect, the invention provides a method of analyzing an amount of affected tissue in a patient diagnosed as potentially suffering an ischemic stroke, the method for quantifying an amount of brain tissue that may have been affected by an ischemic stroke, the method comprising the steps of:
  a) conducting a non-contrast computed tomography (CT) scan of the patient to obtain at least one non-contrast CT image(s);
  b) using a non-transitory computer readable medium encoded with instructions to perform the following steps:
    i) analyzing the non-contrast CT image(s) according to a pre-defined protocol including the steps of:
      i.1 map a plurality of zones of interest;
      i.2 analyze each zone of interest to assign a value to each zone of interest where an assigned value represents dead brain tissue, viable brain tissue or uncertain brain tissue;
      i.3 calculating a provisional score based on a cumulative total of values from step i.2
  c) conducting a multi-phase CT scan of the patient to obtain at least one contrast CT image(s);
  d) using a non-transitory computer readable medium encoded with instructions to perform the following steps:

ii. analyzing the contrast CT image(s) according to a second pre-defined protocol including the steps of:
  ii.1 map a plurality of zones of interest;
  ii.2 analyze each zone of interest to assign a collateral value to each zone of interest where an assigned collateral value represents relative viability of collaterals within that zone and where the assigned value represents dead brain tissue, viable brain tissue or uncertain brain tissue;
  ii.3 calculating a secondary score based on a cumulative total of values from step ii.2.

In one embodiment, the pre-defined protocol is an ASPECTS protocol where the total number of zones of interest is about 10.

In one embodiment, the second protocol includes assigning a collateral value to each zone of interest and the collateral value confirms or alters the assigned value as calculated from step i.2.

In another embodiment, each zone of interest from the non-contrast (first set) and contrast CT (second set) image(s), (collectively opposite sets) is coregistered with a corresponding zone of interest in the opposite set.

In another aspect, the invention provides a method of analyzing an amount of affected tissue in a patient diagnosed as potentially suffering an ischemic stroke, the method for quantifying an amount of brain tissue that may have been affected by an ischemic stroke, the method comprising the steps of: a) conducting a non-contrast computed tomography (CT) scan of the patient to obtain at least one non-contrast CT image(s); b) using a non-transitory computer readable medium encoded with instructions to perform the following steps: analyzing the non-contrast CT image(s) according to a pre-defined protocol including the steps of: i.1 map a plurality of zones of interest; i.2 analyze each zone of interest to assign a value to each zone of interest where an assigned value represents dead brain tissue, viable brain tissue or uncertain brain tissue; i.3 calculating a provisional score based on a cumulative total of values from step i.2; c) conducting a single CT angiogram scan of the patient to obtain at least one contrast CT image(s); d) using a non-transitory computer readable medium encoded with instructions to perform the following steps: ii. analyzing the contrast CT image(s) according to a second pre-defined protocol including the steps of: ii.1 enabling the marking of a prominent venous structure and a prominent artery structure on the at least one image(s); ii.2 measuring a signal in Hounzfield Units of the marked structures from ii.1. and ii.3 determine the density of the prominent venous structure and the prominent artery structure and calculating a secondary score based on the density difference between the prominent venous structure and prominent artery structure.

In another aspect, the invention provides a method of analyzing an amount of affected tissue in a patient diagnosed as potentially suffering an ischemic stroke, the method for quantifying an amount of brain tissue that may have been affected by an ischemic stroke, including the steps of: a) conduct a non-contrast computed tomography (CT) scan on a patient to obtain at least one image(s); b) effect data processing on the at least one image(s) to obtain a provisional ASPECTS according to an ASPECTS protocol, said data processing including the steps of: identify and analyze ASPECTS zones from the at least one image(s); calculate a provisional ASPECTS from step b. i.; c) conduct a contrast computed tomography (CT) scan on a patient to obtain at least one contrast image(s); d) effect data processing on the at least one contrast image(s) to obtain a secondary ASPECTS, said data processing including the steps of: identify and analyze ASPECTS zones from the at least one contrast image(s); calculate collateral scores for each ASPECTS zones from step b. i.; and calculate a secondary ASPECTS score from the collateral scores from step b.ii.

In another embodiment, the method includes the step of comparing the provisional and secondary ASPECTS scores and calculating a confidence level for the secondary ASPECTS score.

In another aspect, the invention provides a method of using at least one contrast image(s) from a multi-phase computed tomography (CT) scan of a patient to calculate ASPECTS comprising the steps of: using a non-transitory computer readable medium encoded with instructions to perform the following steps: analyzing the at least one contrast image(s) including the steps of: i.1 map a plurality of zones of interest on the at least one contrast image(s); i.2 analyze each zone of interest to assign a collateral value to each zone of interest where an assigned collateral value represents relative viability of collaterals within that zone and where the assigned collateral value represents dead brain tissue, viable brain tissue or uncertain brain tissue; and i.3 calculating ASPECTS based on a cumulative total of values from step ii.2.

In one embodiment step i.2. includes comparing corresponding zones on a symptomatic side of the at least one image(s) to the asymptomatic side and analyzing a difference in contrast density between the symptomatic side and the asymptomatic side.

BRIEF DESCRIPTION OF THE DRAWINGS

The invention is described with reference to the accompanying figures in which:

FIG. 5A are images of a multiphase CT (mCTA) scan from a fourth case in accordance with the invention where 3 sets (phases) of image data were obtained over approximately 8 second intervals through the entire brain of the patient; the first row (P1) being first phase data; the middle row (P2) being second phase data and the third row (P3) being third phase data.

DETAILED DESCRIPTION OF THE INVENTION

Figure 1:
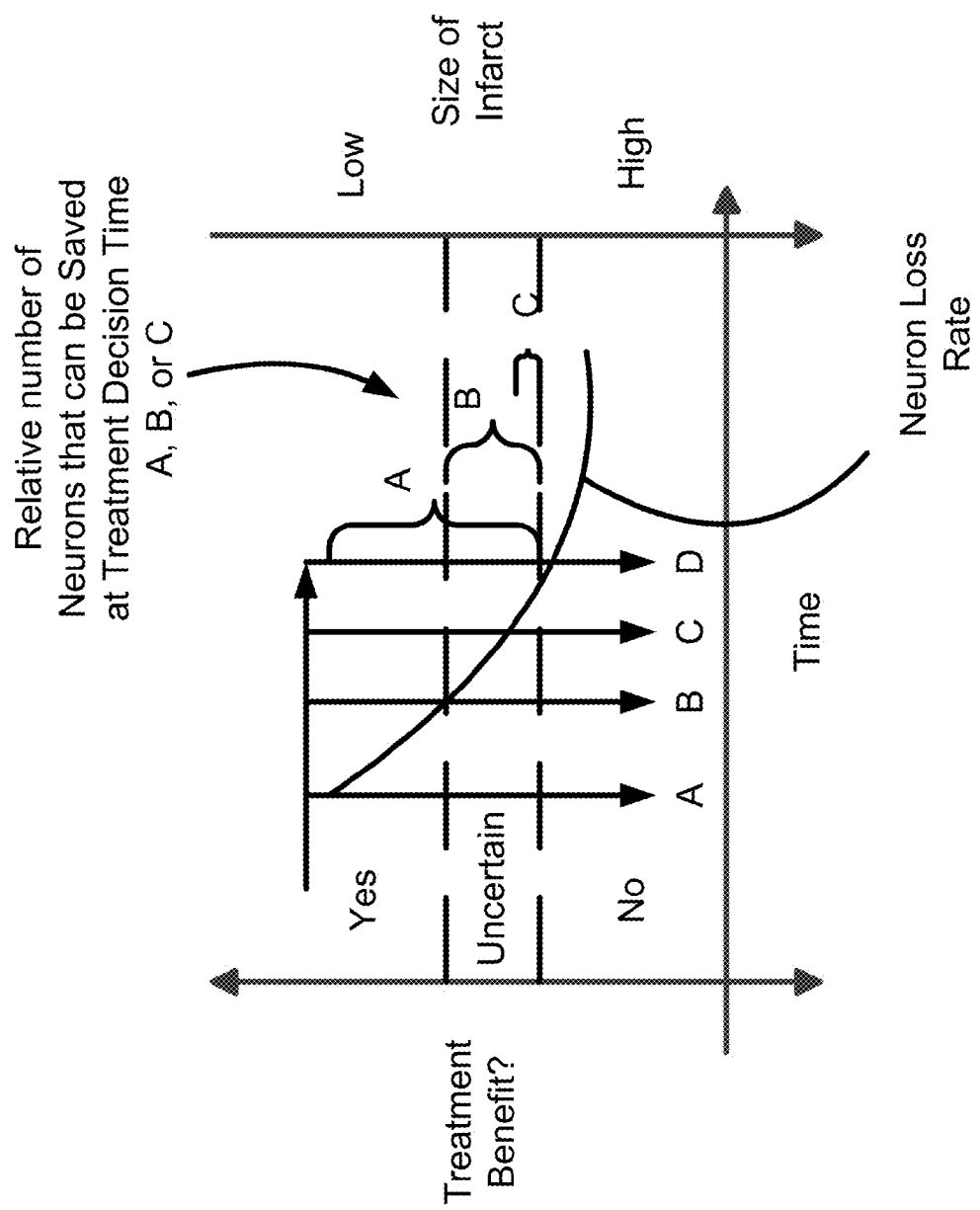
FIG. 1 is a schematic diagram showing the relative effect of the time of a treatment decision to the benefit of a potential treatment with consideration to relative size of an infarct.
Figure 2:
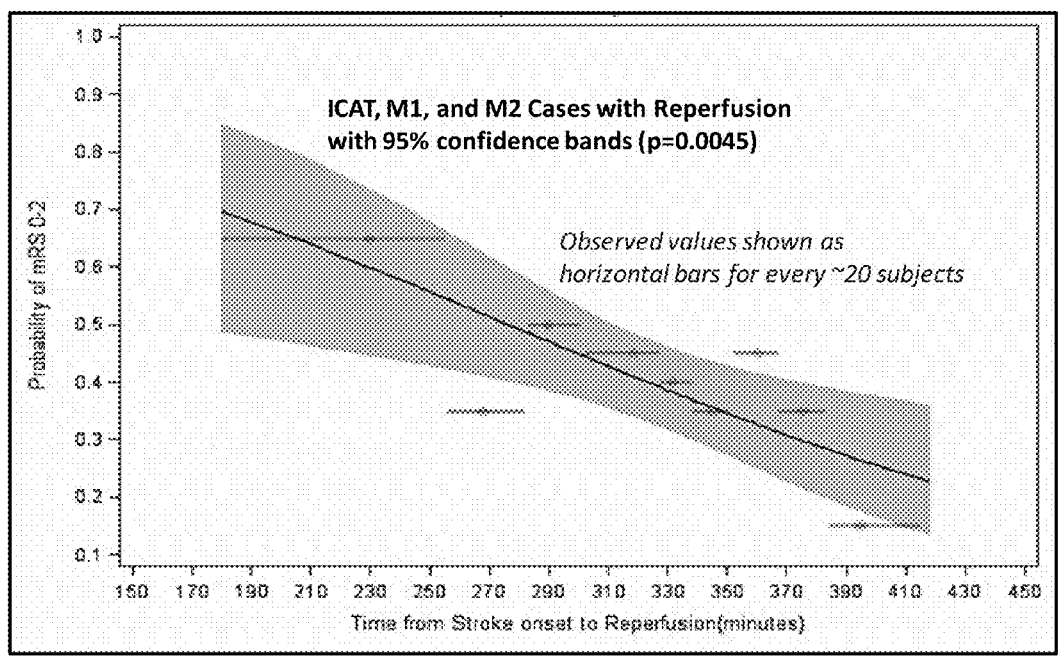
FIG. 2 is a graph showing time to re-perfusion and good clinical outcome.

With reference to the figures, systems and methods for diagnosing strokes are described. More specifically, multi-phase CT (mCTA) angiogram techniques are described that can significantly improve the time required to effect an accurate diagnosis for a stroke patient. Importantly, the procedures described herein allow for faster diagnosis of the location and extent of blockages as well as faster and semi-quantitative determination of the extent of the collaterals which will aid the physician in determining the treatment protocol. The systems and methods of the invention are primarily discussed herein in relation to ischemic strokes but may also be applied to the diagnosis of hemorrhagic strokes as discussed below. The systems and methods of the invention can be used to improve the accuracy and confidence of ASPECTS.

In a first aspect, the invention involves conducting multiple CT angiograms over a condensed period of time and at defined intervals. In a second aspect and from the image information obtained, the location and diameter of collaterals, the density of contrast and variance in the rate of filling of the collaterals (i.e. the rate of opacification) is assessed in both space and time which is used to create a collateral map or collateral score. The collateral map or collateral score can be used by the physician to make a diagnostic and/or treatment decision.

Generally, in the context of this invention, and as explained in greater detail below, a collateral map is a visual representation of multiple, time varied images of a section of the brain that show a variance in contrast over a period of time. A collateral score is a grading system that represents the relative "strength" of collaterals.

In accordance with the first aspect of the invention, mCTA is a multiple image CT procedure conducted with a single bolus of contrast. It is conducted as 3-5 phases of CTA at a 6-12 second (preferably about 8 seconds) interval between each CT scan; however, the time interval may be longer in some circumstances, for example during the work up of hemorrhagic stroke or older patients or in patients with atrial fibrillation resulting in poor cardiac output, may suggest a greater interval. In addition, the time period may be varied between each CT scan. The mCTA procedure produces a series of time-sequenced or phases of images at different levels within the brain that provide information about the flow of contrast through areas of the brain from which the quality of perfusion and the quality of collaterals can be assessed and/or calculated.

Initially, the mCTA methodology is described in comparison to past procedures by way of example for typical cases to illustrate the distinctions between past procedures and some of the treatment scenarios where mCTA can provide significant advantages over these procedures. The following four examples are representative of various diagnostic scenarios that may occur at a treatment center and are intended to illustrate various time situations that could occur in the treatment of typical patients. The numbers and times discussed are not intended to be limiting.

Case 1—CT, CTA, CTP Procedure

A 72 year old man presents to the ER at 0820 hours. On examination, he has right hemiplegia and aphasia with an NIHSS of 19. As known, NIHSS is a stroke scale where the NIHSS number is derived from an examination of the patient. The scale range is from zero to 42 with 42 indicating that the patient is dead. Generally, a score of 10 or larger usually means a large stroke.

A quick examination of the patient is performed (5 min to complete). An IV line is started, blood is withdrawn and the patient is transferred to CT scan. Patient arrives at CT scan at 0840 hours.

A non-contrast CT scan is performed at 0843 hours. This is immediately seen by the treating physician and it does not show a bleed. The CT technologist immediately sets up for doing a CT angiogram. A CT angiogram is performed (80 cc of contrast is injected). The CTA is completed by 0846 hours.

The CT technologist gets set up to do a CT perfusion exam (CTP). A localizer is performed and CTP is started (an additional 45 cc of contrast is injected along with 2000 DLP of radiation exposure). The CTP study is over by 0851.

In the meantime, the CTA data is available for review (while the CTP is going on) by 0848 hours. The treating physician is able to make the following assessments:

1. The patient has an ischemic stroke.
2. Approximate size of core (based on ASPECTS score).
3. Site of occlusion.
4. Quality and quantity of collaterals.

Going back to CTP, the data is transferred to a dedicated workstation. The data is available at the workstation at 0901 hours. An expert initiates and undertakes the required steps of post processing with it being noted that the expert may not be immediately available and may be an additional source of delay. The post processing takes 10 minutes. Finally there is a discussion of interpretation of the final CBF, CBV and MTT maps that takes another 5-7 minutes. The CTP data is finally available at 0918 hours. Thus, the detailed CTP data is available approximately 30 min after the CTA data.

Case 2—CT, mCTA

A 65 year old presents with slight right sided weakness and slight difficulty in word finding. The NIHSS was 4.

Patient is taken for a CT, mCTA. The initial non-contrast CT scan is unremarkable. CT angiogram shows an ulcerated plaque at the origin of the left internal carotid artery. No obvious intracranial occlusion is seen. However on the mCTA there is hold up of contrast in one of the branches of middle cerebral artery (MCA) which is detected on the later phases. This allows for detection of an embolus in the M4 branch (one of the distal branches) of the MCA. This has the potential to alter patient management including prognostication, decision on admission as well as whether or not to give thrombolytics.

Case 3—CT, CTA, mCTA, CTP

A 75 year old woman presents with left hemiplegia at 1520 hours. After assessment the patient is shifted to the CT scan suite. The patient is not cooperative and is not able to hold perfectly still. There is slight amount of motion artifact on the non-contrast CT scan. Some sections have to be repeated. Subsequently, the multiphase CTA is performed. There is again some degree of motion artifact that affects the quality of the scan at the level of the neck and in the second phase. However the intracranial examinations on the first and third phase are of good quality. Subsequently a CTP is performed. However due to patient motion the data is uninterpretable in spite of attempts at motion correction. In this scenario, it is important to note that the uninterpretable data (i.e. marginal data) was not available for consideration until the time the post processing was performed (which as in the example above took approx 30 min beyond the multiphase CTA). The treating team has no choice but to depend on the multiphase CTA or to bring the patient back and do another CTP which is a less desirable protocol as it requires more contrast, more radiation and more time.

Case 4—CT, CTA, CTP

The patient presents at 0220 hours. All the imaging: non contrast CT, CTA and CTP are performed as above. However there is no one available at that time who knows how to do the post processing. The person is paged from home. However the person is not able to do this from home so has to come into the hospital. It produces a delay of over 45 minutes.

mCTA Procedures and Interpretation

Figure 3:
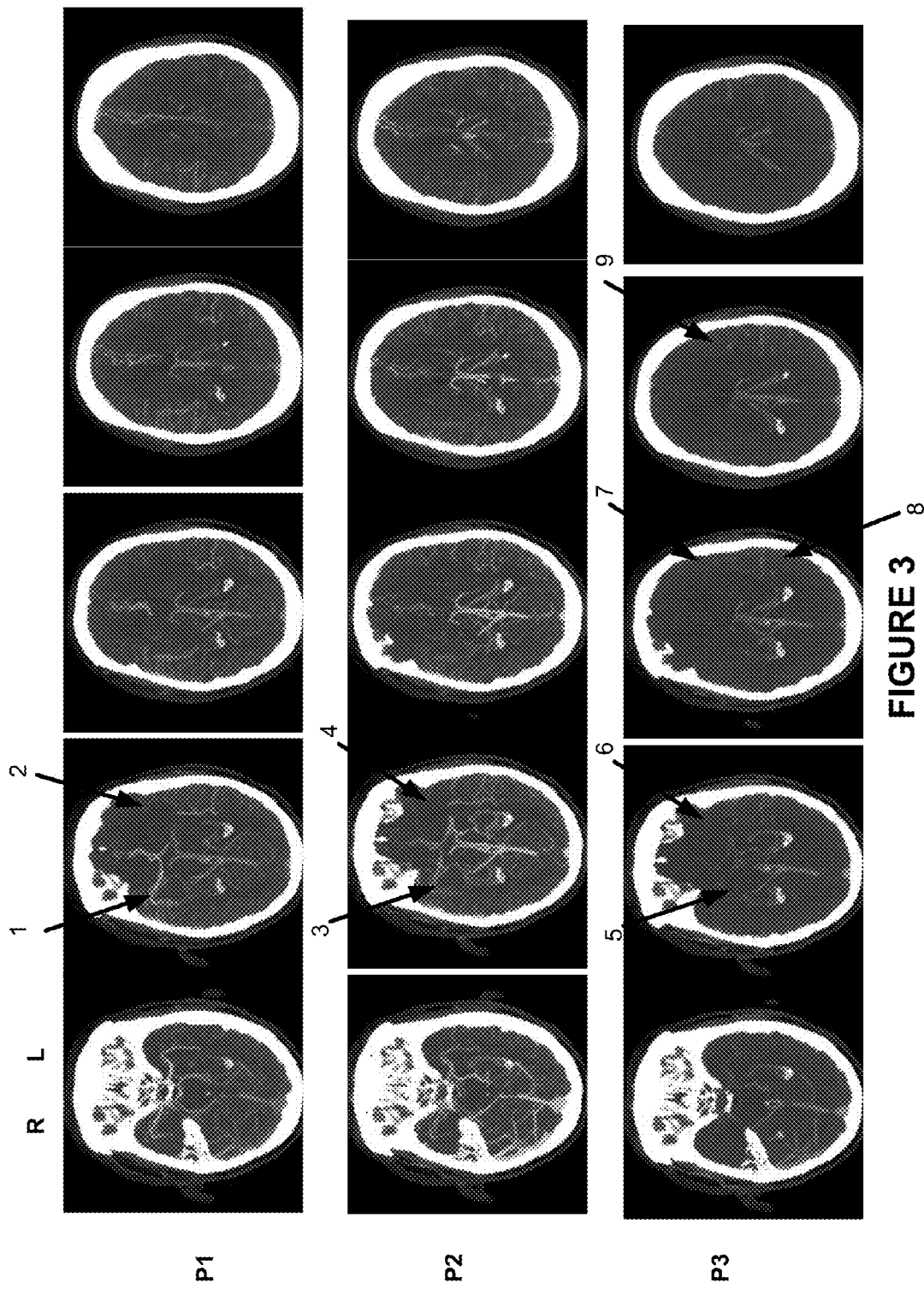
FIG. 3 are images of a multiphase CT (mCTA) scan from a first case in accordance with the invention where 3 sets (phases) of image data were obtained over approximately 8 second intervals through the entire brain of the patient; the first row (P1) being first phase data; the middle row (P2) being second phase data and the third row (P3) being third phase data.

As shown in FIG. 3, representative images from mCTA are described. The top row of images shows a first phase CT scan. More specifically, the first row of images shows 5 different spatial slices of a patient's brain at a first time, referenced herein as phase 1 or P1. The second and third row of images also show 5 corresponding spatial slices of a patient's brain at second and third times or P2 and P3 respectively at the same levels that the P1 images.

From the P1 images, it can be seen that the right side vessels of the brain contralateral to the side causing the patient's symptoms, are unaffected as they can be seen as fully opacified (right middle cerebral artery branches) at P1 (arrow 1) whereas the left side (ipsilateral) is not opacified (arrow 2). In addition, it can be seen that posteriorly (PCA circulation), both sides are unaffected as the vessels are opacified. That is, the P1 scan shows that within a few seconds of injecting a contrast bolus, the contrast has effectively flowed to the anterior right side and the posterior regions of the brain and has otherwise been fully distributed as would be expected within healthy tissue. In comparison, at P1, arrow 2 shows that contrast has not fully perfused an area of the left side by the absence of a similar contrast density as compared to the right side. Thus, these P1 images are suggestive of a left side occlusion.

At P2, on the right side, contrast is passing through the contralateral vessels (arrow 3). Thus, the P2 images show a decreasing contrast density on the healthy right side. At P3, almost all of the contrast has passed and the contrast density is lower still on the right side (arrow 5).

At P2, on the anterior left side, the images show that some collaterals are filling due to an observed increase in contrast density at this level (arrow 4). At P3, the contrast density is increasing further (arrow 6). In addition, at other levels, a hold up of contrast can be seen in the left middle cerebral artery (MCA) region (arrow 7).

From these images, it is determined that the perinsular region (ie. the region where the collaterals are weak (arrows 6, 7, 9)) is at a greater risk to die, whereas posteriorly (arrow 8), the brain may be salvageable.

Accordingly, from this series of time sequenced images, the physician has a basis on which to assess the quality of the collaterals. In this first example, collateral health is sufficiently robust to suggest potentially salvageable tissue and thus in conjunction with the patient's clinical symptoms may make the decision to conduct an intra-arterial recanalization treatment.

It should also be noted and as understood by those skilled in the art that the medical practitioner in making a diagnostic/treatment decision may also be making that decision based on a concurrent evaluation of the non-contrast CT scan (and other clinical data) which has already been performed and/or obtained from the patient.

Figure 4:
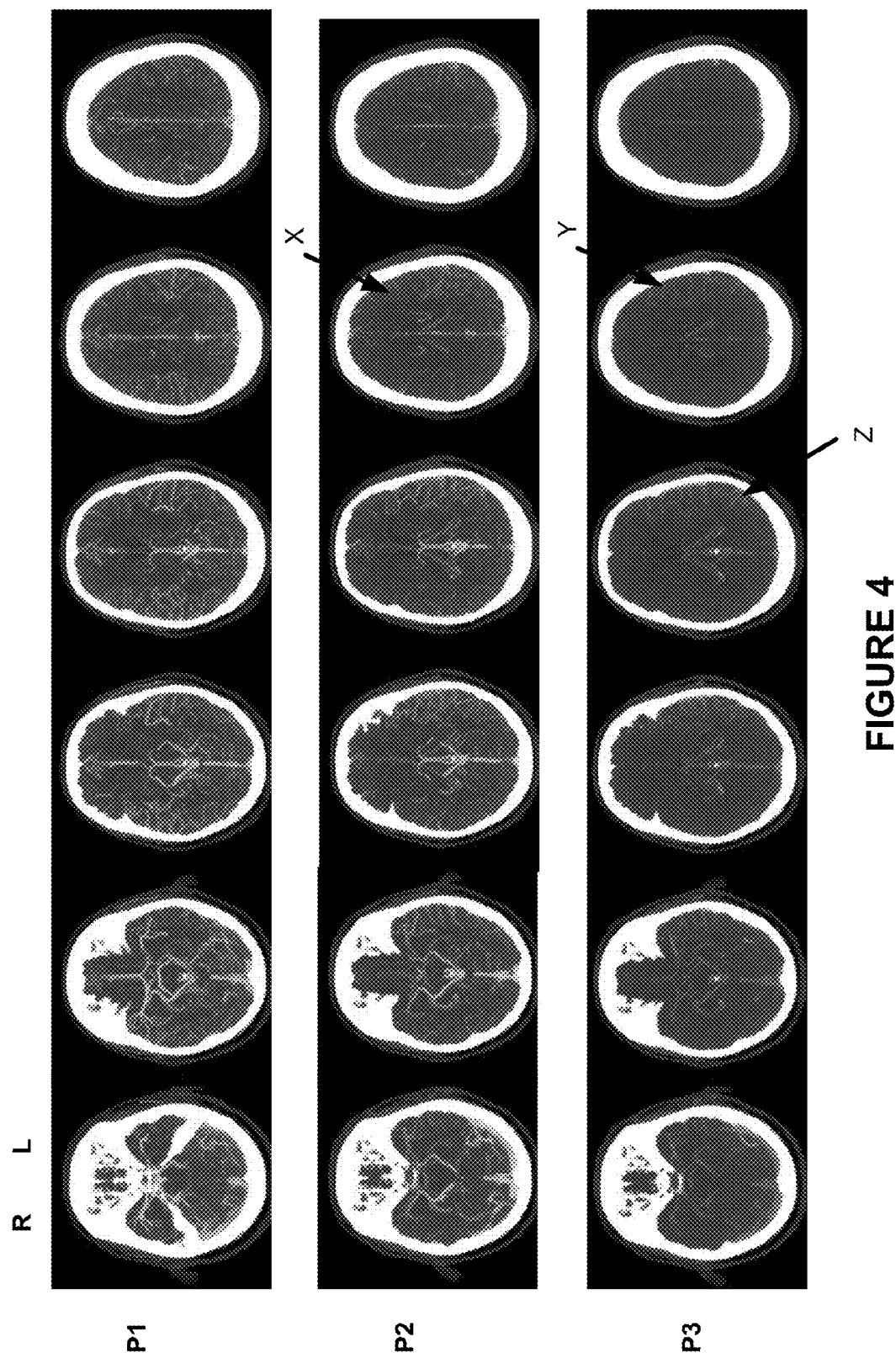
FIG. 4 are images of a multiphase CT (mCTA) scan from a second case in accordance with the invention where 3 sets (phases) of image data were obtained over approximately 8 second intervals through the entire brain of the patient; the first row (P1) being first phase data; the middle row (P2) being second phase data and the third row (P3) being third phase data.

As shown in FIG. 4, the series of images suggest a different treatment. In this case, the original CT scan and the patient's clinical presentation suggested a left side occlusion. The P1 images confirmed a small clot in the left MCA but the P1 images also show relatively robust contrast density in the anterior left side. The P1 right side images similarly show good contrast density. The P2 and P3 right side images show that contrast is clearing as expected for healthy tissue. However, the P2 and P3 images show that contrast is clearing more slowly than on the right side (arrows X, Y, Z). The slow clearing rate shows that the area, while at risk, has excellent collaterals, thus suggesting that nearly all of the left MCA territory is salvageable.

Figure 5:
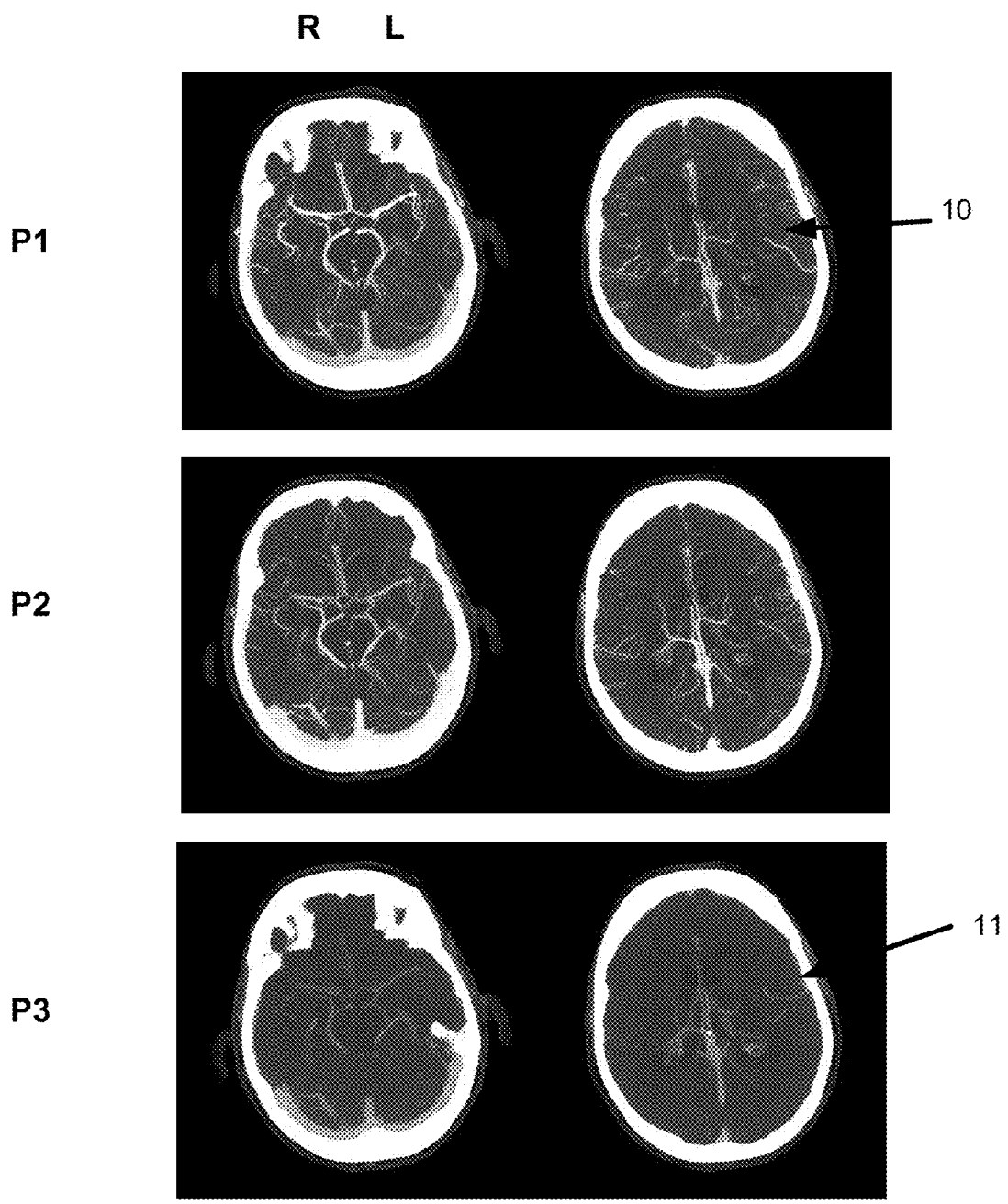
FIG. 5 are images of a multiphase CT (mCTA) scan from a third case in accordance with the invention where 3 sets (phases) of image data were obtained over approximately 8 second intervals through the entire brain of the patient; the first row (P1) being first phase data; the middle row (P2) being second phase data and the third row (P3) being third phase data.

A further case is shown in FIG. 5 where a distal occlusion on the left is observed (arrow 10). Normally, a distal occlusion (i.e. an occlusion within smaller vessels and that cannot be treated by recanalization) is difficult to detect on a routine CT angiogram. However, from the P3 image, it can be observed the contrast is no longer seen in most of the intracranial arteries. However there is still contrast visible in some of the distal left MCA branches (arrow 11) suggesting retrograde filling through collaterals and also points to the site of occlusion. Thus, the mCTA procedure enables the physician to confirm that the patient has had a stroke and may need to be admitted to the treatment facility for further monitoring and/or or treatment.

In FIG. 5A, the three rows represent the three phases P1, P2 and P3 with an approximate 8 second image interval. In the P1 images, the arrow identifies an area with poor opacification in comparison to the posterior regions where there is strong contrast density. These images, when interpreted along with the non-contrast CT scan, also helps in a more accurate and precise determination of infarct core.

In the P3 images which are taken approximately 16 seconds after the P1 images, the arrows show a hold up of contrast in the left MCA territory thus indicating that contrast is filling in through collaterals.

It is important to note that on the right side (normal side), the P3 images show near complete clearing of contrast from the arterial vasculature by the third phase which would be expected as contrast flows through unaffected vessels approximately 16 seconds after injection.

The images collectively indicate that the periinsular region (i.e. the area that shows poor collaterals) is at high risk to die; however further posteriorly and cranially, there are good collaterals likely representing salvageable brain.

Semi-Quantitative and Quantitative Assessment of Collateral Strength

As can be appreciated, the foregoing mCTA methodology provides a unique series of time-sequenced images that can allow the physician to effect a timely diagnosis of the nature of an ischemic stroke.

In a second aspect of the invention, methods of providing a quantitative or semi-quantitative assessment of collateral strength are described that are built from the mCTA images.

As described above, the mCTA procedures provide data that is sequenced in time. The image data can be interpreted based on different input functions including:

a. Change in contrast density of the entire brain over time.
b. Change in contrast density of vessels over time.
c. Rate of opacification of vessels beyond the occlusion.
d. Comparison of contrast density to the opposite side of the brain (eg. not an absolute change in contrast density but a comparison to a corresponding area of the opposite side of the brain),
e. Location of the occlusion. For example, for an M1 occlusion (proximal middle cerebral artery), collaterals come through leptomeningeal connections from the anterior cerebral artery and posterior cerebral artery while for an M2 occlusion (first order branch of the middle cerebral artery) collaterals come from the other M2 branch.
f. Diameter of vessels distal to the occlusion compared to the contralateral side.
g. Understanding the information on the multiphase CTA taking into account the patient's clinical information eg. a patient with minor stroke symptoms with an MCA occlusion likely has excellent collaterals. However assessment of these collaterals may help determine which patients are likely to deteriorate.

The creation of collaterals maps can in various embodiments take combinations of these input functions into account.

For example, in one example, image data is processed to quantify changes in density in both space and time. The rate of change of density is quantified that then becomes a quantitative measure of the normalcy of circulation (or not).

Figure 6:
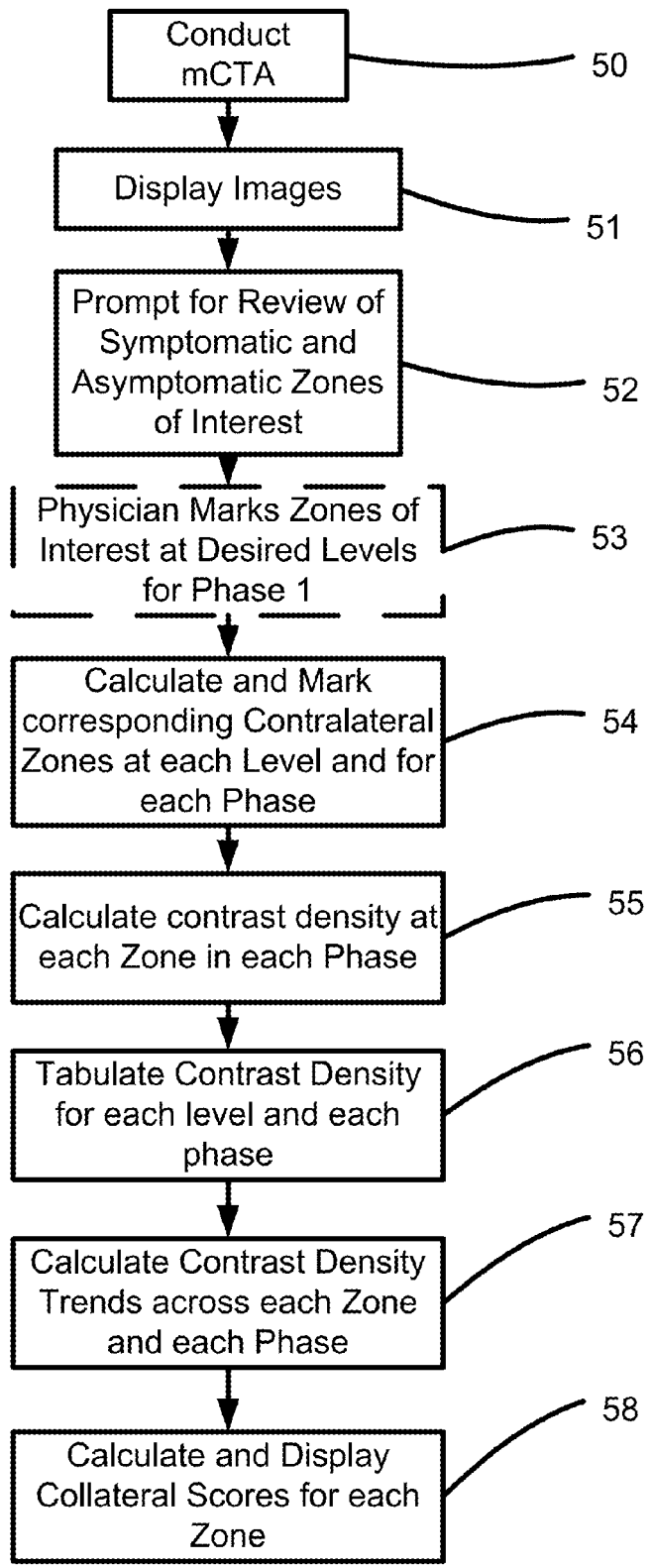
FIG. 6 is a flow-chart showing the steps in creation of a semi-quantitative collateral map in accordance with one embodiment of the invention.

As shown in FIG. 6, a representative algorithm is described that can be used to provide a semi-quantitative assessment of collateral strength from the mCTA images. For each of the images from each of the phases, blood vessel (BV) opacification can be quantified for assisting in making a semi-quantitative assessment of collateral strength.

Figure 6A:
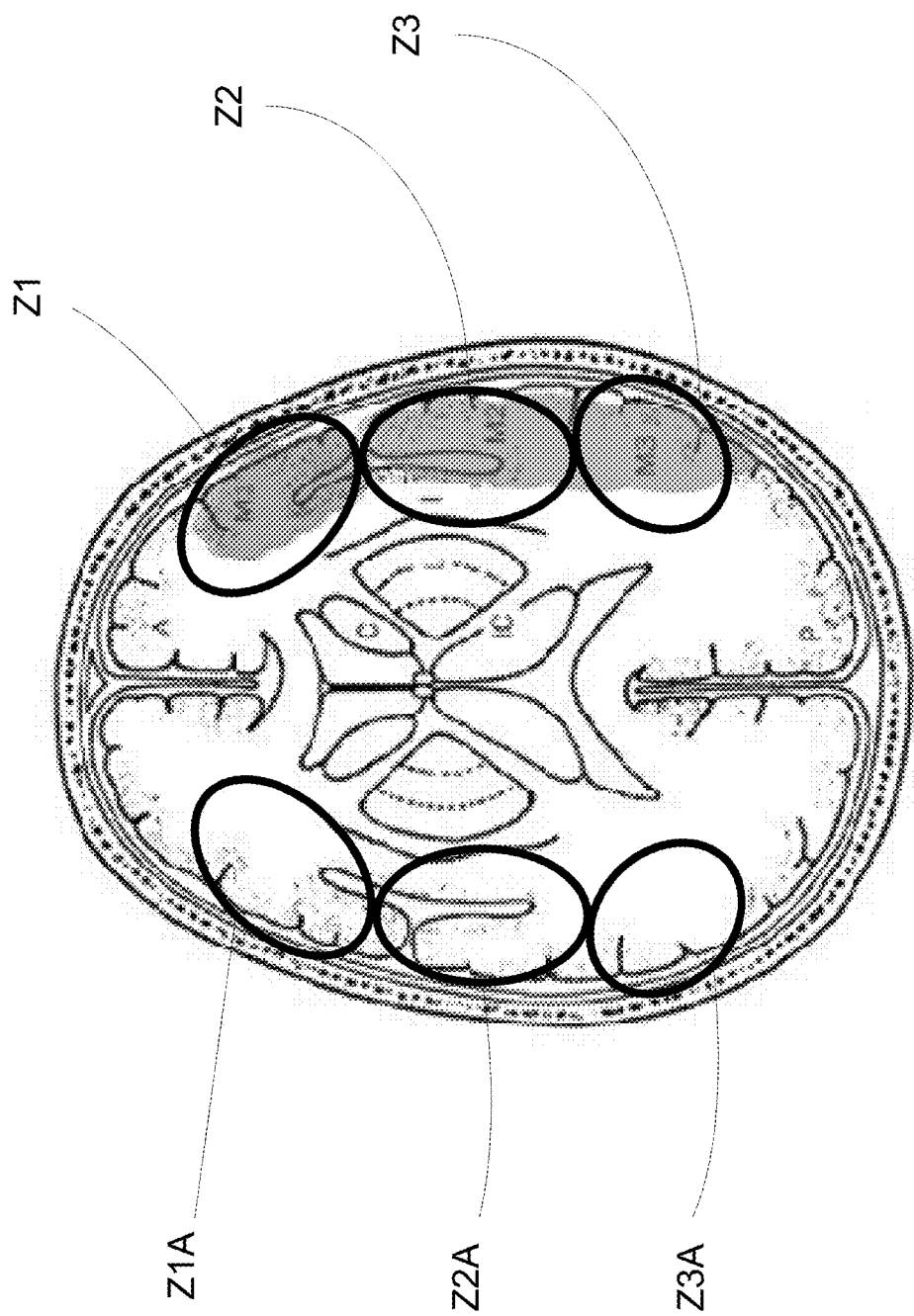
FIG. 6A is a representative image showing how zones of interest may be marked within an mCTA image.

In one embodiment, mCTA software displays the mCTA images 51 to the physician. For the P1 images, the physician is prompted to mark zones of interest including contralateral (asymptomatic) and ipsilateral (symptomatic) regions 52. For the ipsilateral regions, one or more areas from one or more levels showing abnormal perfusion are selected 53. Once marked for P1, the software may automatically identify corresponding areas on the P1-Pn images for the corresponding levels 54 for each phase. The software may enable that corresponding areas on the contralateral side are marked automatically based on the area and location marked for the ipsilateral regions or the physician may mark the ipsilateral zones of interest manually. As shown in FIG. 6A, three ipsilateral zones Z1, Z2, Z3 may be marked on the left side with corresponding areas on the right side, Z1A, Z2A, Z3A being marked for our example.

For the marked P1 areas (Z1-Z3 and Z1A-Z3A), a base measurement of the contrast density is calculated 55. For example, the total area of the zone of interest may be calculated and within that area, the area of vessels containing contrast may be determined based on a color threshold value. That is, the total number of pixels have a threshold darkness is determined, thus providing a base value of contrast density. For the P2-Pn images, the same contrast measurements/calculations are made for the corresponding areas. These values may be tabulated by the software 56.

In healthy tissue, it would normally be expected that the degree of opacification would decrease from P1-Pn as contrast is passing through the vessels for the typical contrast injection volume and the time period between each phase. Thus, a rate of decrease in contrast can be calculated to provide a determination of the behavior of healthy tissue. In one embodiment, this comparison can be compared against typical or known rates of contrast as may be stored in a database.

Similarly, in the ipsilateral region, areas of interest can be similarly marked for each of the P1-Pn images. In the ipsilateral region, different behaviors can be quantified and thereafter compared to the contralateral region to determine a score representing collateral quality 57. It should be noted that it is more likely that the ipsilateral regions of interest are marked initially.

In an example of a case where there may be a severe blockage with poor collaterals, the area of interest may show a low value of contrast at P1 and no change in the calculated contrast density for each successive image. The combination of low P1 contrast density and the absence of change may be indicative of no collateral perfusion in which case the software would flag the area with a low viability value.

For the case of a blockage with acceptable collaterals, the area of interest may show a low value of contrast at P1 but improved or increasing calculated contrast density for each successive image. Thus, in this case, the combination of low P1 contrast density and a positive increase in calculated contrast density may be indicative of acceptable collateral perfusion in which case the software would flag the area with a higher viability value.

Table 4 shows representative values that the software may utilize in calculating collateral scores after the practitioner has marked the zones of interest. In this example, the practitioner suspects a left side occlusion based on images as shown in FIG. 4. As described above, the P1 images confirmed a small clot in the left MCA but the P1 images also show relatively robust contrast density in the anterior left side. The P1 right side images similarly show good contrast density. The P2 and P3 right side images show that contrast is clearing as expected for healthy tissue. However, the P2 and P3 images show that contrast is clearing more slowly than on the right side (arrows X, Y, Z).

As shown in Table 4, the software may tabulate the data derived from the mCTA images and the areas that have been marked. These are representative values only as an indicator of relative numbers for the purposes of illustration only.

TABLE 4

Representative Area and Contrast Density Values for Zones of Interest.

| Zone of Interest | Area (mm$^2$) | P1 Contrast Density (1-10) | P2 Contrast Density (1-10) | P3 Contrast Density (1-10) | Comment |
|---|---|---|---|---|---|
| Z1 | 20 | 5 | 5 | 4 | Primary Area of Interest |
| Z2 | 20 | 7 | 5 | 4 | Secondary |
| Z3 | 10 | 8 | 5 | 4 | Secondary |
| Z1A | 20 | 8 | 6 | 2 | Healthy tissue |
| Z2A | 20 | 8 | 6 | 2 | Healthy tissue |
| Z3A | 10 | 8 | 6 | 2 | Healthy tissue |

Table 5 shows how tabulated data may be used to calculate either a qualitative or quantitative value related to contrast density in the various zones of interest. For the purposes of illustration below, qualitative values are provided, however, it is understood that specifically calculated values could be derived from the data using appropriate scaling factors. In addition, the parameters of clearance trend rate, contralateral density comparison and clearance time shift are only representative of parameters that may be utilized. For example, in one embodiment, vessel diameter in a zone of interest may be calculated.

TABLE 5

Representative Parameters derived from mCTA

| Zones of Interest | Clearance Trend Rate | Contralateral Density Comparison from P1 to Pn | Clearance Time Shift- Contralateral v. Ipsilateral? | Comment |
|---|---|---|---|---|
| Z1 | Slow | Lower | Yes | Suggests retrograde filling of collaterals |
| Z2 | Medium | Slightly Lower | Minimal | |
| Z3 | Fast | Same | No | Healthy Tissue |

As images are taken from different levels, the software may also consider the effects occurring at different levels.

Color coding of the rate of change of contrast density may be used to provide the physician with a readily identifiable visual indicator of the relative tissue health. For example, the contralateral region may be marked with shades of red indicating healthy perfusion. The ipsilateral region may be marked with color shades ranging from blue (indicating ischemic tissue) to red or green (indicating healthy tissue).

Figure 7:
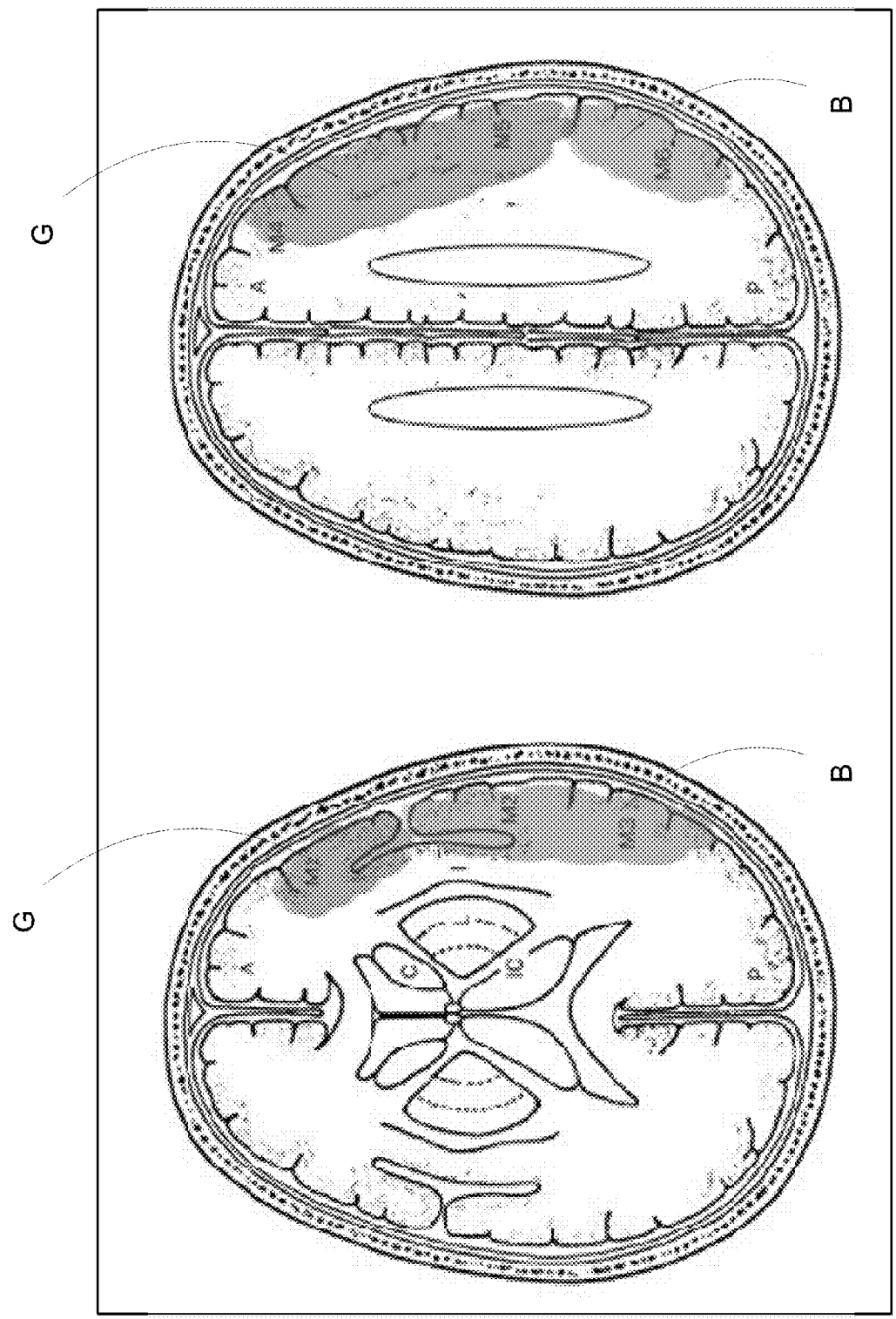
FIG. 7 is a schematic diagram showing segregation of regions of the brain (MCA territory) divided into areas traditionally supplied by ACA collaterals and by PCA collaterals. Ischemic tissue is marked B and healthy tissue marked A.

With reference to FIG. 7, further details of a methodology of assessing collaterals is described by the mCTA technique and specifically the technique being used to identify retrograde filling pial arteries in the MCA territory distal to the occlusion. Pial arteries are distinguished from veins based on morphology, direction of filling and whether visualized early or late. These retrograde filling pial arteries are divided into 2 groups based on origin from anterior or posterior circulation; namely Anterior cerebral artery (ACA) to MCA and Posterior cerebral artery (PCA) to MCA and assessed for the following 2 properties using a grading system:

a) Prominence of pial arteries when compared to similar vessels in the opposite MCA territory (Same or more prominent=2, thin=1, minimal or not visualized=0) on any of the phases.

b) Rate of retrograde filling from parasagittal region to the sylvian sulcus. (Sylvian sulcus filling in first phase=2, in second phase=1, in third phase or not at all=0).

In case of a proximal M2 MCA segment occlusion, the same scoring template is used either in the anterior or in the posterior MCA regions depending on whether a dominant anterior or posterior M2 segment is occluded.

A scoring template as above results in a 4 point score for collateral assessment in the anterior and posterior MCA regions individually. A total score of 0-1 will be considered poor collateral status, 2 will be considered moderate and 3 good and 4 excellent collateral status for M2 MCA+/− intracranial ICA occlusions. A score of 0-2 will be considered poor collateral status, 3-4 will be considered moderate and 5-6 good collateral and 7-8 excellent status for patients with M1 MCA+/− intracranial ICA occlusions. For imaging selection, recanalization in any patient with poor collateral status in either anterior or posterior MCA regions (score 0-1) is likely futile.

Image quality may also be assessed. A good first phase is when convexity pial arteries are well seen on the contralateral asymptomatic hemisphere. If patient factors like congestive cardiac failure, atrial fibrillation, hypotension or contralateral proximal ICA stenosis or technical factors like early triggering of scan acquisition relative to contrast bolus injection limit visualization of convexity pial arteries in the first phase on the contralateral asymptomatic hemisphere, then this scan is considered sub-optimal. However, collateral assessments may still be carried out if the third phase on the contralateral asymptomatic hemisphere is in the late venous phase. If not, this scan cannot be used for collateral assessment. One easy solution for this is to add additional phases.

FIG. 7 also shows representative leptomeningeal collaterals assessed on multi-phase CT-angio at baseline by comparing size and rate of retrograde backfilling in the anterior (G, green) and posterior (B, blue) MCA regions. Any patients with a score 0-1 in either region may not benefit from recanalization therapy. That is, the green, G territory is usually the area of the MCA territory that would be supplied by the ACA when M1 segment (proximal MCA) is blocked. The blue, B territory is the area that would usually be supplied by the PCA in a similar clinical situation.

When an area has a poor collateral score as discussed above, this will mean either the tissue is already dead or the tissue is about to die and would be dead by the time the vessel can be opened making it a case of futile recanalization.

The hardware and software to enable mCTA requires modification of known CT imaging equipment to enable the display of the images to the physician (and/or technicians) and to enable practitioners to input appropriate markings to the images for subsequent calculations. That is, the system provides appropriate computer input systems for point, line or shape marking for the purposes of identifying and/or delineating points, areas or zones of interest. Appropriate scales are supported to enable consistent comparison between marked areas on an images and comparisons across patients. Back end computer systems, user interfaces and network configurations enable the effective support for the various computational algorithms and the sharing or distribution of data across both local and wide area networks.

Discussion

Importantly, the mCTA techniques as described above provide numerous advantages over currently used CTA and CTP procedures in the diagnosis of ischemic stroke.

mCTA can be done utilizing any CTA scanner (with appropriate software modifications as necessary) and thus significantly increases the number of centers where more efficient stroke diagnosis can be achieved. In addition, mCTA does not require the same degree of post-processing as currently required by CTP; does not require additional contrast to be injected into the body; and subjects the body to less radiation as compared to a CTA procedure that is followed by a CTP procedure.

That is, although mCTA may utilize an additional 2-4 phases of radiation (as compared to CTA alone) where the patient is subjected to an additional ~150-200 dose length product (DLP) per phase, this is less than what the patient would be subjected to by a CTP procedure where the total amount of radiation may be 1800-4000 DLP. Generally, the additional phases of mCTA will add up to around 0.6-0.9 of a head CT scan dose or 600-900 DLP.

Importantly, the mCTA data that is collected over the typical 3-5 cycles provides the physician will a sequential series of data that can reveal changes in density within the collateral network over a known period of time.

Intravascular Clot/Thrombus Identification and Quantification

In another aspect of the invention, blood clots causing an ischemic stroke and parameters describing the clot can be determined from appropriate graphical user interface and the addition of further processing algorithms as described below.

That is, in proximal artery occlusion it is helpful to the endovascular surgeon to understand more about the nature of the clot causing the stroke. In particular, it is useful to know the exact length of the clot and its relative permeability. These parameters can be difficult to determine using traditional CTA where only the proximal end of the clot can be identified. Moreover, this information cannot usually be obtained on the CTP images without a detailed study of the source images that be quite time consuming. The mCTA procedures allows for a quick determination of this length (and/or other dimensional parameters) which has implications in decision making such as choosing the length of the clot retrieving stents (eg. stentriever length) at the time of the recanalization procedure.

In addition, the degree of porosity or permeability of the clot may have implications on the response to intravenous thrombolytic therapy.

The porosity and permeability of a clot can be determined using similar marking procedures as described above. That is, as the contrast goes through the body it will penetrate the clot based on its porosity and permeability and result in a change in density of the clot. As with the other mCTA diagnostic methodologies discussed above, the clot length can be identified and its length determined on the sequential phases of the mCTA. More specifically, as the contrast agent encounters the clot, depending on the porosity and permeability of the clot, the contrast agent will begin to permeate through the clot. Over successive mCTA phases, the images will show an increase in contrast density at the clot site that will not clear due to the hold up of contrast within the clot. This will be likely be seen at different levels as the clot will likely not be planar with the plane of a CT image. Thus, the physician will likely see the growth of contrast density across different levels that is indicative of the clot size and density. As above, the physician may be able to mark the proximal and distal termini of the clot as zones of interests whereby the computational algorithms may utilize a Cartesian coordinate system within the software to estimate clot length and/or other dimensional parameters. Points, areas or zones of interest relating to a clot may be utilized.

In addition, to the extent that contrast permeates relatively quickly through the clot, the rate of permeation may be quantifiable which can be helpful to the physician to the extent that the permeation rate correlates to the ability of the thrombolytic drug to penetrate the clot. This knowledge may be used to effect faster recanalization.

Carotid Artery Occlusion

In another aspect, the systems and methods can be applied to the diagnosis of carotid artery occlusions. Differentiating neck and intra-cranial occlusions can be difficult to diagnose using a CTA procedure as in a contrast CTA procedure a carotid artery occlusion may prevent the appearance of any contrast in the brain from a single series of images. However, by utilizing a mCTA procedure, the successive series of images may be helpful in determining the nature of the occlusion as being neck or intra-cranial as the mCTA procedure may show slow forward filling of the carotid artery in the neck if it is not occluded in successive phases that enables the effective determination of the location of the occlusion.

Hemorrhagic Stroke

In addition, while the foregoing has been described primarily as a technique for obtaining information about ischemic stroke, the technique can also be used in patients with hemorrhagic stroke to determine if there is an active leak from a vessel, whether there is hematoma growth and/or determining the size of the active leak. In the case of hemorrhagic stroke, the mCTA procedure can be utilized to obtain a series of images specifically intended to provide the physician with information about a potential hemorrhagic stroke.

Figure 8:
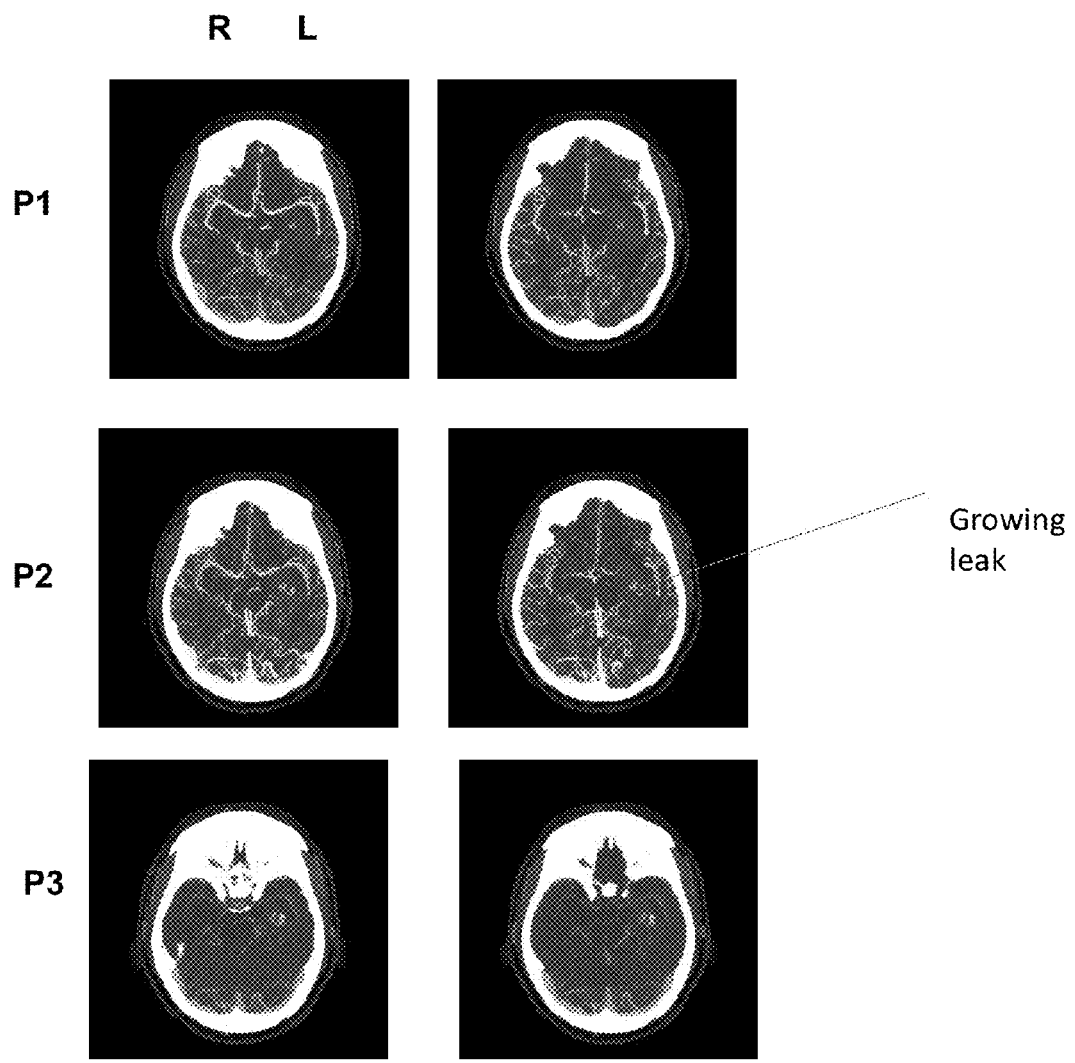
FIG. 8 are images of a multiphase CT (mCTA) scan from a case where the patient has suffered a hemorrhagic stroke. The image data were obtained over approximately 12 second intervals through the entire brain of the patient; the first row (P1) being first phase data; the middle row (P2) being second phase data and the third row (P3) being third phase data.
Figure 8A:
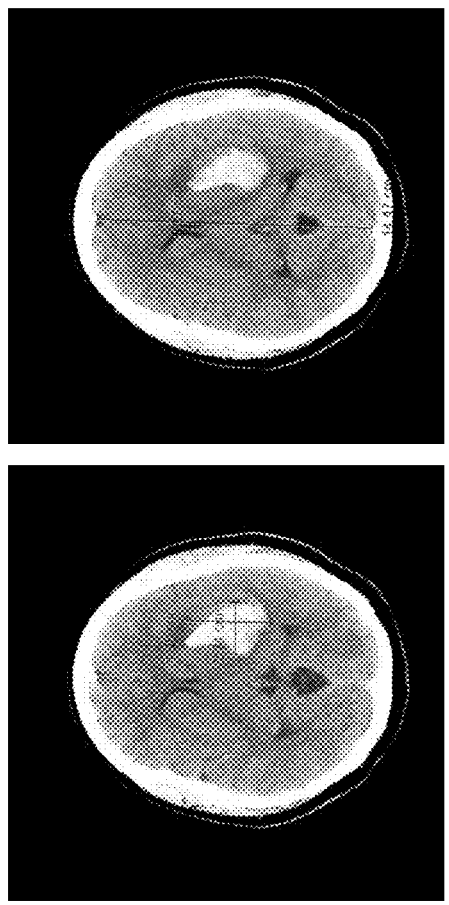
FIG. 8A are initial pre-mCTACT images (no contrast) from the patient of FIG. 6 showing that the patient has suffered a hemorrhagic stroke.
Figure 8B:
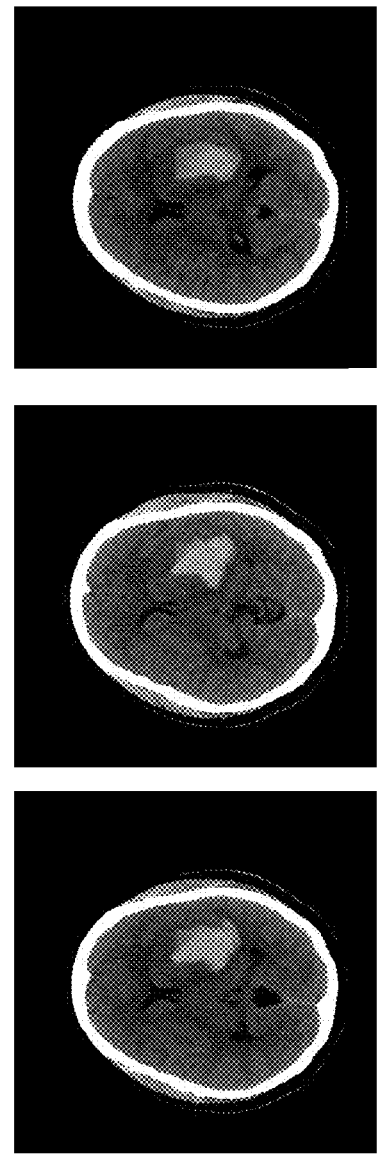
FIG. 8B are follow-up and post-mCTA CT images (no contrast) from the patient of FIG. 6 showing that the size of the hematoma has grown as compared to the images of FIG. 6A.

As shown in FIG. 8, the P1 images are not unusual in that the contrast is seen to arrive as expected on both the contralateral and ipsilateral sides. However, in P2, the contrast is seen to diffuse from the leak side and thus is not clearing as expected in comparison to the contralateral side. The P3 images show that the gradual disappearance of contrast on the ipsilateral side. These images, together with any initial pre-mCTA CT images (no contrast) taken to initially diagnose a hemorrhagic stroke can both confirm a hemorrhagic stroke has occurred but also provide quantitative information about the rate of change in the bleed and other parameters. FIGS. 8A and 8B show initial (no contrast) and follow-up CT images (no contrast; 10 hours later).

Thus, the mCTA methodology is also an effective diagnostic tool for hemorrhagic stroke.

During the mCTA procedure, as noted above, if the patient is suspected of suffering a hemorrhagic stroke, a time t between successive phases of imaging will be selected and will generally be longer relative to an ischemic stroke diagnosis. That is, in a hemorrhagic stroke, the time period of interest is longer and therefore, the multiphase images are obtained over a longer time period. However, the number of phases does not need to be increased. Typically, if hemorrhagic stroke is suspected, each phase will be conducted at a 10-40 second interval, with 10-30 seconds as a more typical interval.

ASPECTS

In another aspect mCTA is utilized to automate ASPECTS and/or improve the confidence in ASPECTS that may have been determined from manual, semi-automatic or automatic means. As noted, under existing protocols ASPECTS is determined from non-contrast CT evaluation of two standardized regions of the MCA territory: the basal ganglia level, where the thalamus, basal ganglia, and caudate are visible, and the supraganglionic level, which includes the corona radiata and centrum semiovale. To compute ASPECTS, 1 point is subtracted from 10 for any evidence of early ischemic change for each of the 10 defined regions that contribute to the ASPECTS.

Importantly, from non-contrast CT, ASPECTS is determined from a measure of the amount of dead brain tissue (or not). However, it does not consider a collateral score that may be derived from mCTA or other contrast imaging. As such, past ASPECTS techniques attempting to automate the determination of ASPECTS using only non-contrast CT data does not consider scenarios where the collaterals may affect ASPECTS and/or is only able to make a "best guess" as to what that score may be. That is, and importantly, there are scenarios where a patient has a low (or uncertain) ASPECTS but good collaterals and similarly scenarios where the patient has a high ASPECTS but poor collaterals. As such, without correlation to a collateral score, the confidence a physician may have in ASPECTS calculated by a computer is affected and hence, the confidence in making a treatment decision is affected.

By introducing mCTA data and a collateral score derived from mCTA, confidence in ASPECTS can be increased.

Figure 9:
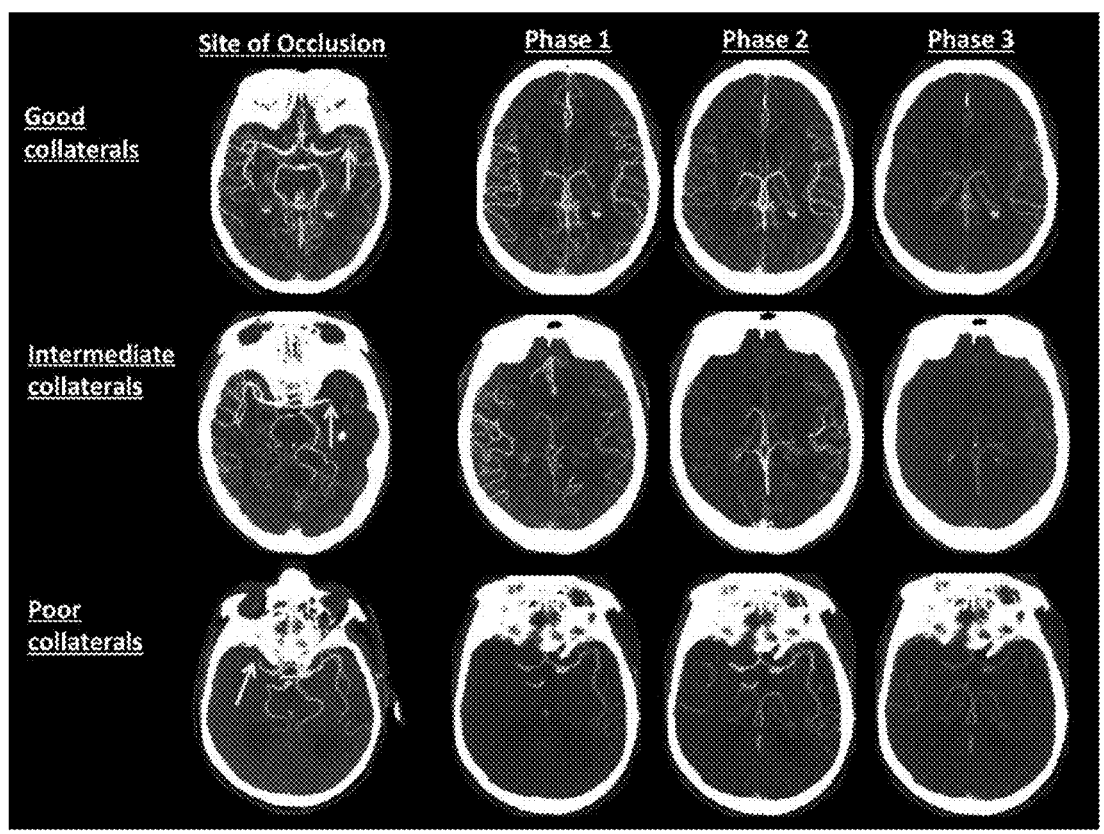
FIG. 9 are mCTA images where the upper panel shows a patient with a left M1 MCA occlusion (arrow) and good collaterals (backfilling arteries) on multi-phase CTA. The middle panel shows a patient with a left M1 MCA occlusion (arrow) and intermediate collaterals and the lower panel shows a patient with a right M1 MCA occlusion (arrow) and poor collaterals (minimal backfilling arteries) on multi-phase CTA.

FIG. 9 is a series of representative mCTA images where the upper panel shows a patient with a left M1 MCA occlusion (arrow) and good collaterals (backfilling arteries) on multi-phase CTA. The middle panel shows a patient with a left M1 MCA occlusion (arrow) and intermediate collaterals and the lower panel shows a patient with a right M1 MCA occlusion (arrow) and poor collaterals (minimal backfilling arteries) on multi-phase CTA. Such images can be analyzed as a means to improve the accuracy and confidence of ASPECTS.

As described above, collaterals are measured on multi-phase CTA by comparing backfilling arteries beyond the blocked artery to similar arteries in the opposite unaffected hemisphere. Vascular enhancement distal to an occlusion is analyzed and scored in anterior and posterior MCA territories to obtain a collateral score as shown in Table 6.

TABLE 6

Collateral Score Determination/Algorithm from mCTA Data

| Category | Score | Description |
| --- | --- | --- |
| Good | 5 | Compared to asymptomatic contralateral hemisphere, there is no delay and normal or increased prominence of peripheral vessels/normal extent within the occluded arteries territory within the symptomatic hemisphere. |
|  | 4 | Compared to asymptomatic contralateral hemisphere there is a delay of one phase in filling in of peripheral vessels but prominence and extent is the same. |
| Intermediate | 3 | Compared to asymptomatic contralateral hemisphere there is a delay of two phases in filling in of peripheral vessels but prominence and extent is the same or there is a one phase delay and decreased prominence (thinner vessels)/reduced number of vessels in some part of the territory occluded. |
|  | 2 | Compared to asymptomatic contralateral hemisphere there is a delay of two phases in filling in of peripheral vessels and decreased prominence and extent or a one-phase delay and some regions with no vessels in some part of the territory occluded. |

TABLE 6-continued

Collateral Score Determination/Algorithm from mCTA Data

| Category | Score | Description |
| --- | --- | --- |
| Poor | 1 | Compared to asymptomatic contralateral hemisphere there are just a few vessels visible in any phase within the occluded vascular territory. |
|  | 0 | Compared to asymptomatic contralateral hemisphere there are no vessels visible in any phase within the occluded vascular territory. |

*On a single phase, multiphase or dynamic CTA: no or minimal collaterals in a region greater than 50% of the MCA territory when compared to pial filling on the contralateral side can also be considered as poor collaterals.

That is, according to the Table 6 algorithm, multiphase CTA allows a much more precise determination of collaterals that is based on 3 different factors:
   a. Density of collaterals.
   b. How quickly the collaterals opacify.
   c. How quickly the contrast clears out of the collaterals.

Based on these, the collaterals can be graded on a scale of e.g. 0-5 such that 0 is absent collaterals; 1: poor collaterals; 2 moderate collaterals 3. Good collaterals 4. Very good collaterals and 5 excellent collaterals. Also these can be regionally calculated using the same brain atlas map as what is used for ASPECTS determination.

In other words, using a brain mapping algorithm, every cortical region of ASPECTS can also have a collateral score from the multiphase CTA utilizing mCTA data with the result being that ASPECTS can be automated by correlating the collateral score from mCTA with ASPECTS score from non-contrast CT.

In one embodiment, following acquisition of mCTA data, the physician is prompted to mark potentially affected zones at the levels according to the generalized ASPECTS protocol. That is, as the ASPECTS protocol requires evaluation of the basal ganglia level, and the supraganglionic level, the software presents these levels of images to the physician for marking according to the general ASPECTS protocols. However, it is preferable that no marking is required and the algorithms automatically determine and analyse the particular zones of the brain for ASPECTS from the images.

Based on the marked (or automatically determined) areas and subsequent processing, the computer arrives at a collateral score (see Table 6 rules).

In the clinical situation where time is important, and the reliability of data on which the physician is making a decision is also important, analysis or consideration of "rough" data followed by "precise" data can lead to better decisions.

Accordingly, the subject methodology is preferably a two step process where a provisional ASPECTS is first calculated from non-contrast CT which is then followed by calculation of a secondary ASPECTS that uses mCTA data which provides a more accurate ASPECTS.

For example, a provisional ASPECTS from non-contrast CT may have be calculated as 8 based on the non-contrast CT data showing affected M1, M2 regions (i.e two zones). The subsequent acquisition and analysis of mCTA data may determine a collateral score to be good in 8 of 10 zones (eg. 4-5) thus giving the physician confidence that the original ASPECTS of 8 is valid. Conversely, if the collateral score is poor (eg. 0-1) in 4 of 10 zones, the two sets of data would be considered to be out of sync, such that the physician will have less confidence in the original ASPECTS and hence, prompt them to consider additional factors that may have contributed to the reliability of the original ASPECTS and/or to conduct additional study.

Similarly, if the original ASPECTS is low (eg. 4) and the collateral score is low, the data would be considered to be in sync and the confidence in the original ASPECTS would be high.

Accordingly, mCTA data provides a method to improve the confidence a physician may have with ASPECTS thus leading to better reliability in diagnostic and treatment decisions.

Figure 10:
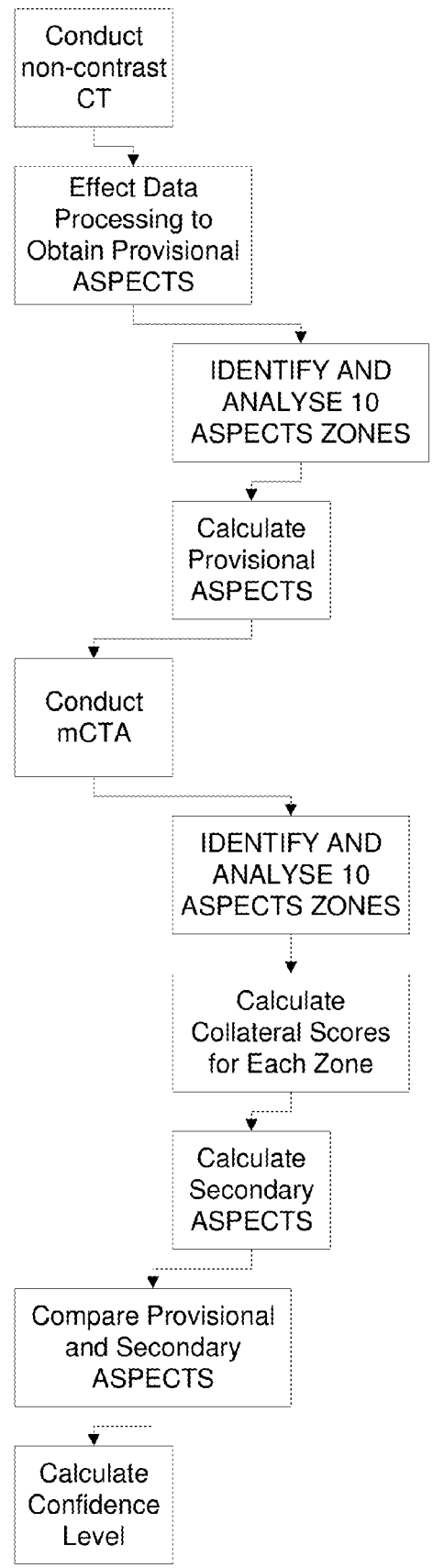
FIG. 10 is a flowchart showing representative steps for calculating ASPECTS using both non-contrast CT and contrast CT data.

In furtherance of the above, and in accordance with a representative methodology, the following steps are completed (see FIG. 10):

a. Acquire CT head data (i.e. a non-contrast CT scan)
b. Effect data processing of CT head data to provisional ASPECTS algorithm (PAA).
c. Apply PAA to provide provisional ASPECTS. The PAA utilizes the non-contrast CT data to a) determine the ASPECTS zones of the CT scan (i.e. the 10 ASPECTS zones) and b) within each zone calculate a provisional ASPECTS within that zone. That is, after determining the ASPECTS zones, the PAA will, based on color/density thresholds (amongst other factors) determine whether the tissue within a zone warrants ASPECTS of 0 or 1. By conducting this calculation within each of the 10 zones a provisional score between 0-10 is obtained. However, it is noted that the PAA may not be able to confidently determine if a zone is a 0 or 1 and hence, may assign 0.5 to that zone indicating uncertainty. If a single zone is marked as uncertain, and two zones are marked as zero, the provisional ASPECTS would be 7-8 (i.e two dead zones and 1 uncertain zone). Similarly, if there are 4 uncertain zones and 2 dead zones, the provisional ASPECTS would be 4-8. Importantly, the greater the range (i.e uncertainty), the less valuable the data is for making a confident decision.
d. At a time, during steps b, or c, or after d acquire mCTA data. That is, conduct a contrast mCTA procedure to obtain mCTA data.
e. Effect data processing of mCTA data to secondary ASPECTS algorithm (SAA);
f. Coregister mCTA images to plain CT head images. Coregistration involves matching corresponding slices of mCTA and CT head data with each other such that corresponding areas/regions of one image are paired. Once paired, the defined ASPECTS zones of each can be analyzed and/or compared as representing a similar area. For example, the M1 region of both images would be defined by a coregistration algorithm as having the same area in each image, thus enabling a comparison/analysis of each zone from each data source individually and with one another.
g. Determine collateral score from mCTA data and specifically ASPECTS for each of the 10 defined ASPECTS regions. That is, the collateral score in M1 may be calculated as 4 from the mCTA data (as per Table 6) and hence for the purposes of determining ASPECTS, the M1 score would be 1. This is repeated for each of the 10 zones to calculate a secondary ASPECTS.
h. Compare provisional ASPECTS to secondary ASPECTS and calculate a confidence level of the secondary ASPECTS based on the provisional ASPECTS. For example, if the provisional ASPECTS is 4-8, the physician is confident that two of 10 zones are dead but there is uncertainty about 4 of the 10 zones. Thus, there is a high degree of uncertainty in the provisional ASPECTS. If, in this scenario, the secondary ASPECTS is calculated as 7, the physician is more confident that the uncertain zones are in fact alive and can more confidently make a treatment decision. Similarly, if the provisional and secondary ASPECTS are both 8, the confidence level is high that the true clinical situation is presenting itself. Importantly, the SAA considers known clinical scenarios wherein with the completion of additional analysis as outlined above, reduces the number of possibilities and hence, increases the confidence for the physician that the score being presented represents the clinical situation.
i. In addition, in one embodiment, the SAA will identify those regions where there may be uncertainty and prompt the physician to review those regions. That is, the SAA enables the physician to review the CT data in combination with the mCTA data for any region (i.e. by the coregistration) and allows the physician to change or confirm the regional score. For example, if the physician sees good collaterals in a region (i. e. a good, very good or excellent collateral score of 3-5) but sees uncertain data from the CT scan, the physician can mark the tissue as alive thus not deducting an ASPECTS point. Similarly, if the collateral score is 0-2 (ie absent, poor or moderate) and the CT scan data is uncertain, the physician can confirm the tissue is substantially or completely dead, mark it as such and confirm that an ASPECTS point should be deducted.

Hence, the system allows the physician to more precisely determine ASPECTS with a higher degree of confidence.

It should be noted that the above method could be followed using single phase CTA. While using just a single phase of contrast images within the SAA would not provide as much information as more than one phase of contrast images, it would be better than not utilizing any contrast CTA data. Hence, the above methodology contemplates a single phase of mCTA data.

For example, the physician can grade collaterals from a single phase CTA under some scenarios (i.e from a single set of contrast images). In one example, the signal intensity of a big vein (e.g. superior sagittal sinus), can be evaluated wherein if it is dense enough, the physician can conclude that enough time has elapsed and that the collaterals, if present would have filled in. Said steps can include enabling the marking of a prominent venous structure and a prominent artery structure on the at least one contrast image(s); measuring a signal in Hounzfield Units of the marked arterial and venous structures and determining the density of the prominent venous structure and the prominent artery structure and calculating a secondary score based on the density difference between the prominent venous structure and prominent artery structure.

Although the present invention has been described and illustrated with respect to preferred embodiments and preferred uses thereof, it is not to be so limited since modifications and changes can be made therein which are within the full, intended scope of the invention as understood by those skilled in the art.

REFERENCES (1) Khatri P, Yeatts S D, Mazighi M, Broderick J P, Liebeskind D, Demchuk A, Amarenco P, Foster L D, Goyal M, Hill M D, Palesch Y, Jauch E, Haley E C, Tomsick T A. Time To Angiographic Reperfusion is Highly Associated with Good Clinical Outcome in the IMS III Trial. Presented at the International Stroke Conference, Honolulu, Hi., 2013.
(2) Broderick J P, Palesch Y Y, Demchuk A M, Yeatts S D, Khatri P, Hill M D, Jauch E C, Jovin T G, Yan B, Silver F L, von Kummer R, Molina C A, Demaerschalk B M, Budzik R, Clark W M, Zaidat O O, Malisch T W, Goyal M, Schonewille W J, Mazighi M, Engelter S T, Anderson C, Spilker J, Carrozzella J, R T R, Ryckborst K J, Janis L S, Martin R H, Foster L D, Tomsick T A; the Interventional Management of Stroke (IMS) III Investigators. *Endovascular Therapy after Intravenous t-PA versus t-PA Alone for Stroke*. N Engl J Med. 2013 Feb. 7.
(3) Time is brain—quantified. Stroke. 2006 January; 37(1): 263-6. Epub 2005 Dec. 8.
(4) 2015 AHA/ASA Focused Update of the 2013 Guidelines for the Early Management of Patients With Acute Ischemic Stroke Regarding Endovascular Treatment A Guideline for Healthcare Professionals From the American Heart Association/American Stroke Association http://stroke.ahajournals.org/content/early/2015/06/26/STR.0000000000000074

The invention claimed is:

1. A method of analyzing an amount of affected tissue in a patient diagnosed as potentially suffering an ischemic stroke, the method for quantifying an amount of brain tissue that may have been affected by an ischemic stroke, the method comprising the steps of:
   a) conducting a non-contrast computed tomography (CT) scan of the patient to obtain at least one non-contrast CT image(s);
   b) using a non-transitory computer readable medium encoded with instructions to perform the following steps:
      i. analyzing the non-contrast CT image(s) according to a pre-defined protocol including the steps of:
         i.1 map a plurality of zones of interest;
         i.2 analyze each zone of interest to assign a value to each zone of interest where an assigned value represents dead brain tissue, viable brain tissue or uncertain brain tissue;
         i.3 calculating a provisional score based on a cumulative total of values from step i.2
   c) conducting a single or multi-phase CT angiogram scan of the patient to obtain at least one contrast CT image(s);
   d) using a non-transitory computer readable medium encoded with instructions to perform the following steps:
      ii. analyzing the contrast CT image(s) according to a second pre-defined protocol including the steps of:
         ii.1 map a plurality of zones of interest;
         ii.2 analyze each zone of interest to assign a collateral value to each zone of interest where an assigned collateral value represents relative viability of collaterals within that zone and where the assigned collateral value represents dead brain tissue, viable brain tissue or uncertain brain tissue;
         ii.3 calculating a secondary score based on a cumulative total of values from step ii.2.

2. The method as in claim 1 where the pre-defined protocol is an Alberta Stroke Program Early CT Score (ASPECTS) protocol.

3. The method as in claim 2 where the total number of zones of interest is 10.

4. The method as in claim 1 where the second protocol includes assigning a collateral value to each zone of interest and the collateral value confirms or alters the assigned value as calculated from step i.2.

5. The method as in claim 4 where zones of interest are cortical zones.

6. The method as in claim 1 where each zone of interest from the non-contrast (first set) and contrast CT (second set) image(s), (collectively opposite sets) is coregistered with a corresponding zone of interest in the opposite set.

7. A method of analyzing an amount of affected tissue in a patient diagnosed as potentially suffering an ischemic stroke, the method for quantifying an amount of brain tissue that may have been affected by an ischemic stroke, the method comprising the steps of:
   a) conducting a non-contrast computed tomography (CT) scan of the patient to obtain at least one non-contrast CT image(s);
   b) using a non-transitory computer readable medium encoded with instructions to perform the following steps:
      i. analyzing the non-contrast CT image(s) according to a pre-defined protocol including the steps of:
         i.1 map a plurality of zones of interest;
         i.2 analyze each zone of interest to assign a value to each zone of interest where an assigned value represents dead brain tissue, viable brain tissue or uncertain brain tissue;
         i.3 calculating a provisional score based on a cumulative total of values from step i.2
   c) conducting a single CT angiogram scan of the patient to obtain at least one contrast CT image(s);
   d) using a non-transitory computer readable medium encoded with instructions to perform the following steps:
      ii. analyzing the contrast CT image(s) according to a second pre-defined protocol including the steps of:
         ii.1 enabling the marking of a prominent venous structure and a prominent artery structure on the at least one image(s);
         ii.2 measuring a signal in Hounzfield Units of the marked structures from ii.1;
         ii.3 determine the density of the prominent venous structure and the prominent artery structure and calculating a secondary score based on the density difference between the prominent venous structure and prominent artery structure.

8. A method of analyzing an amount of affected tissue in a patient diagnosed as potentially suffering an ischemic stroke, the method for quantifying an amount of brain tissue that may have been affected by an ischemic stroke, the method comprising the steps of:
   a. conduct a non-contrast computed tomography (CT) scan on a patient to obtain at least one image(s);
   b. effect data processing on the at least one image(s) to obtain a provisional Alberta Stroke Program Early CT Score (ASPECTS) according to an ASPECTS protocol, said data processing including the steps of:
      i. identify and analyze ASPECTS zones from the at least one image(s);
      ii. calculate a provisional ASPECTS from step b. i.;
   c. conduct a contrast computed tomography (CT) scan on a patient to obtain at least one contrast image(s);
   d. effect data processing on the at least one contrast image(s) to obtain a secondary ASPECTS, said data processing including the steps of:

i. identify and analyze ASPECTS zones from the at least one contrast image(s);
   ii. calculate collateral scores for each ASPECTS zones from step b. i.;
   iii. calculate a secondary ASPECTS score from the collateral scores from step b.ii.

9. The method as in claim 8 further comprising the step of comparing the provisional and secondary Alberta Stroke Program Early CT Score (ASPECTS) scores and calculating a confidence level for the secondary ASPECTS score.

10. A method of using at least one contrast image(s) from a multi-phase computed tomography (CT) scan of a patient to calculate Alberta Stroke Program Early CT Score (ASPECTS) comprising the steps of:
   using a non-transitory computer readable medium encoded with instructions to perform the following steps:
   i. analyzing the at least one contrast image(s) including the steps of:
   i.1 map a plurality of zones of interest on the at least one contrast image(s);
   i.2 analyze each zone of interest to assign a collateral value to each zone of interest where an assigned collateral value represents relative viability of collaterals within that zone and where the assigned collateral value represents dead brain tissue, viable brain tissue or uncertain brain tissue and compare corresponding zones on a symptomatic side of the at least one image(s) to the asymptomatic side and analyzing a difference in contrast density between the symptomatic side and the asymptomatic side;
   i.3 calculating ASPECTS based on a cumulative total of values from step i.2 for quantifying an amount of brain tissue that may have been affected by an ischemic stroke.

* * * * *